United States Patent
Hirao et al.

(10) Patent No.: US 10,550,393 B2
(45) Date of Patent: Feb. 4, 2020

(54) METHOD FOR STABILIZING DNA APTAMERS

(71) Applicant: TAGCYX BIOTECHNOLOGIES, Meguro-ku, Tokyo (JP)

(72) Inventors: Ichiro Hirao, Tokyo (JP); Michiko Hirao, Tokyo (JP); Kenichiro Matsunaga, Saga (JP)

(73) Assignee: Tagcyx Biotechnologies, Tokyo (JP)

( * ) Notice: Subject to any disclaimer, the term of this patent is extended or adjusted under 35 U.S.C. 154(b) by 0 days.

(21) Appl. No.: 15/555,496

(22) PCT Filed: Mar. 4, 2016

(86) PCT No.: PCT/JP2016/056805
§ 371 (c)(1),
(2) Date: Sep. 1, 2017

(87) PCT Pub. No.: WO2016/143700
PCT Pub. Date: Sep. 15, 2016

(65) Prior Publication Data
US 2018/0346912 A1    Dec. 6, 2018

(30) Foreign Application Priority Data
Mar. 6, 2015 (JP) ................................ 2015-045266

(51) Int. Cl.
*C12N 15/115* (2010.01)
*C12N 5/00* (2006.01)

(52) U.S. Cl.
CPC ........ *C12N 15/115* (2013.01); *C12N 2310/16* (2013.01); *C12N 2310/33* (2013.01); *C12N 2310/334* (2013.01); *C12N 2310/336* (2013.01); *C12N 2310/51* (2013.01); *C12N 2310/531* (2013.01); *C12N 2320/51* (2013.01); *C12N 2320/52* (2013.01)

(58) Field of Classification Search
None
See application file for complete search history.

(56) References Cited

U.S. PATENT DOCUMENTS

| 2011/0263459 A1* | 10/2011 | Borer ................. | C12N 15/1048 506/16 |
| 2011/0306653 A1* | 12/2011 | Hirao ................. | A61K 31/7088 514/44 A |
| 2014/0256794 A1 | 9/2014 | Hirao et al. | |

FOREIGN PATENT DOCUMENTS

| EP | 2562257 A1 | 2/2013 |
| EP | 2743349 A1 | 6/2014 |
| EP | 2781599 A1 | 9/2014 |
| WO | WO 2006/033854 A2 | 3/2006 |
| WO | WO 2008/150495 A2 | 12/2008 |
| WO | WO 2009/011855 A2 | 1/2009 |
| WO | WO 2011/132672 A1 | 10/2011 |
| WO | WO 2013/058306 A1 | 4/2013 |

OTHER PUBLICATIONS

Seela et al., Nucleosides, Nucleotides, and Nucleic Acids, vol. 24:855-858, 2005.*
Hirao et al., NAR vol. 20:3891-3896, 1992.*
Hroa et al., Biochinnie vol. 145:15e21, 2018.*
Matsunaga et al., "Architecture of high-affinity unnatural-base DNA aptamers toward pharmaceutical applications," Scientific Reports, Dec. 2015, 5:1-7.
Young, Howard, "Aptamers as New Tools for Inhibiting Cytokine Activity," 3rd International Conference and Exhibition on Clinical & Cellular Immunology, Sep. 29, 2014, 25 pages.
Saiki, Yurina, "Modification of DNA aptamer using unnatural base or mini-hairpin," 2014 Yokohama City University Department of Medical Life Science Master degree thesis presentation, Feb. 18, 2015, 12 pages, with English Translation.
International Search Report and Written Opinion in application PCT/JP2016/056805 dated May 17, 2016 with English translation.
Supplementary European Search Report dated Jul. 13, 2018, in EP 16761670.5.
Diafa et al., "Generation of Aptamers with an Expanded Chemical Repertoire," Molecules, Sep. 14, 2015, 20(9):16643-16671.
Kimoto et al., "Generation of high-affinity DNA aptamers using an expanded genetic alphabet," Nature Biotechnology, Apr. 7, 2013, 31(5):453-457.
Nishikawa et al., "A shRNA library constructed through the generation of loop-stem-loop DNA," The Journal of Gene Medicine, Oct. 29, 2010, 12(11):927-933.
Taylor et al., "Towards applications of synthetic genetic polymers in diagnosis and therapy," Current Opinion in Chemical Biology, Oct. 3, 2014, 22:79-84.
Office Action dated Sep. 25, 2018 in JP 2017-505304.

* cited by examiner

*Primary Examiner* — Sean McGarry
(74) *Attorney, Agent, or Firm* — Foley & Lardner LLP

(57) ABSTRACT

An object of the present invention is to provide a convenient and low-cost method for enhancing the stability of a DNA aptamer and/or its capacity to bind to a target molecule, and a DNA aptamer obtained by the method.
The object is solved by substituting an internal hairpin structure (stem-loop structure) of the DNA aptamer with a structure called mini-hairpin structure and optionally increasing GC pairs in a stem portion of the DNA aptamer.

7 Claims, 24 Drawing Sheets

Specification includes a Sequence Listing.

Fig. 1
(A)
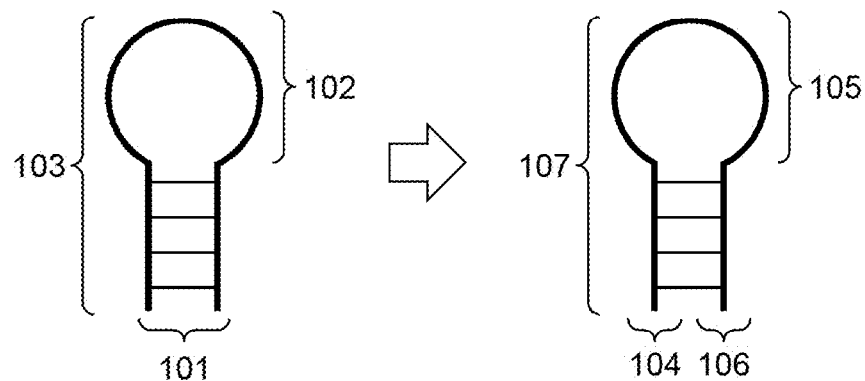
(B)
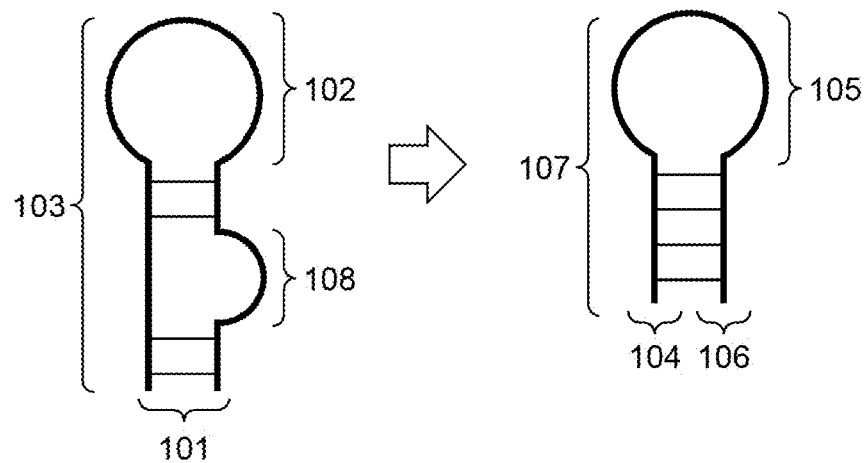
(C)
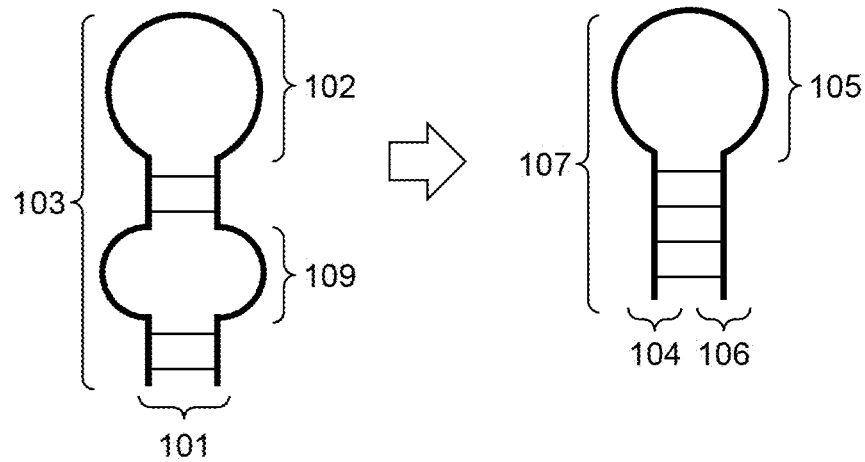

Fig. 2
(A) 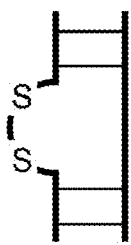  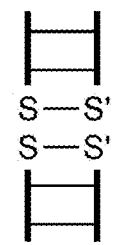
(B)  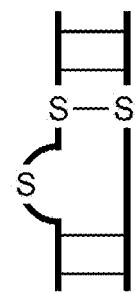

Fig. 11
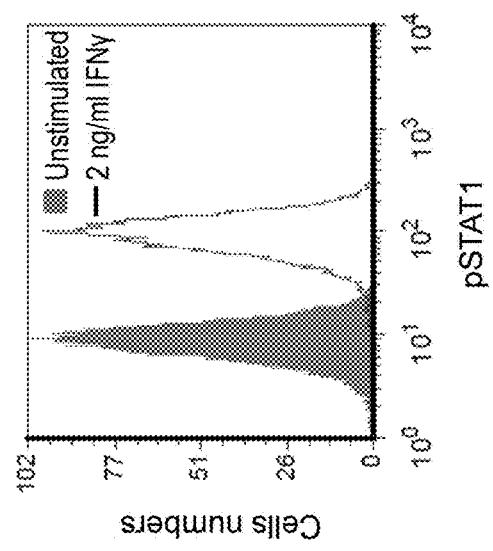
(C)
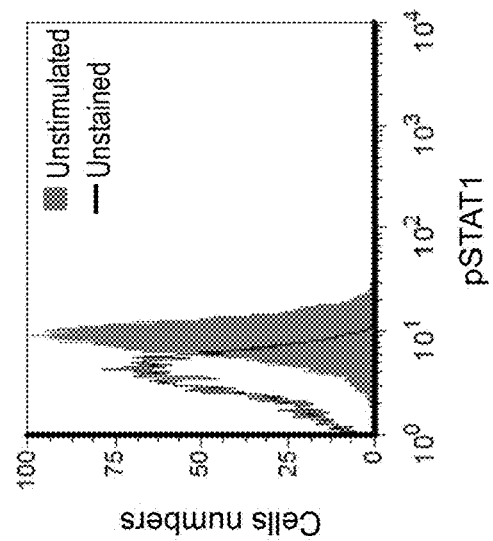
(B)
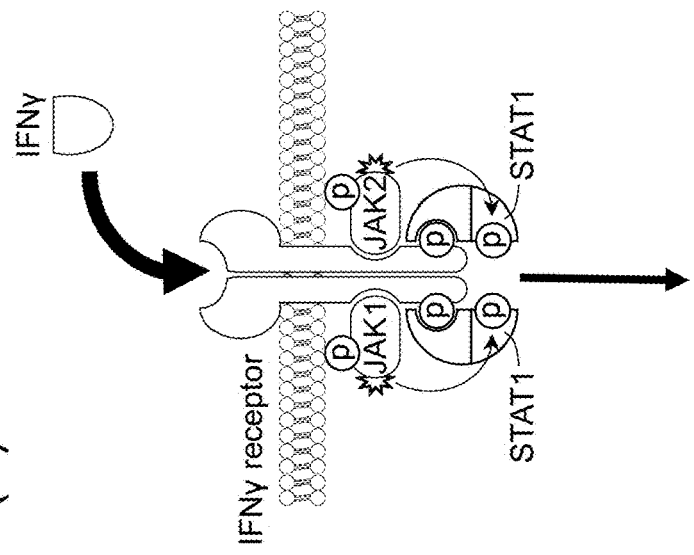
(A)

Fig. 16
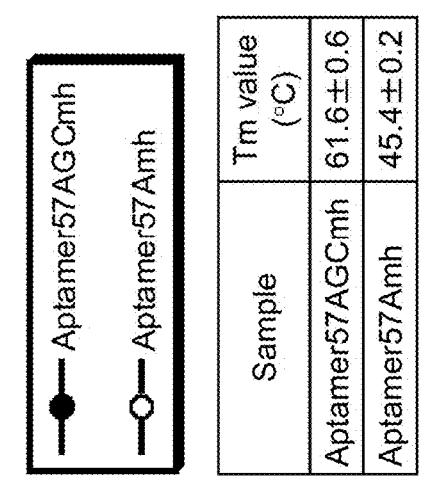
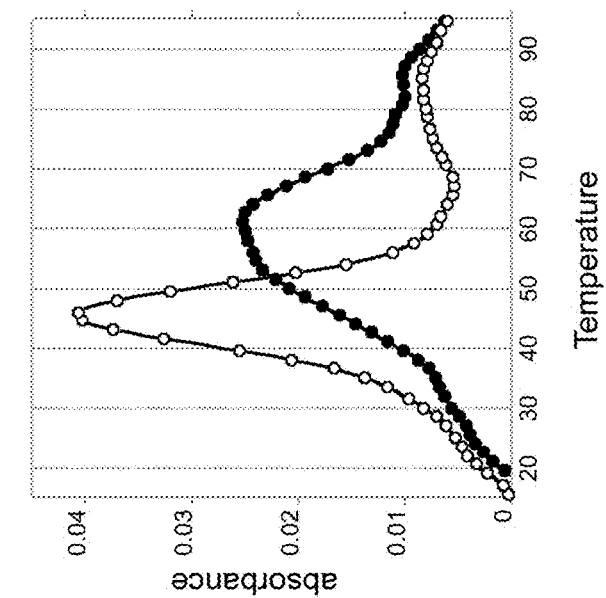
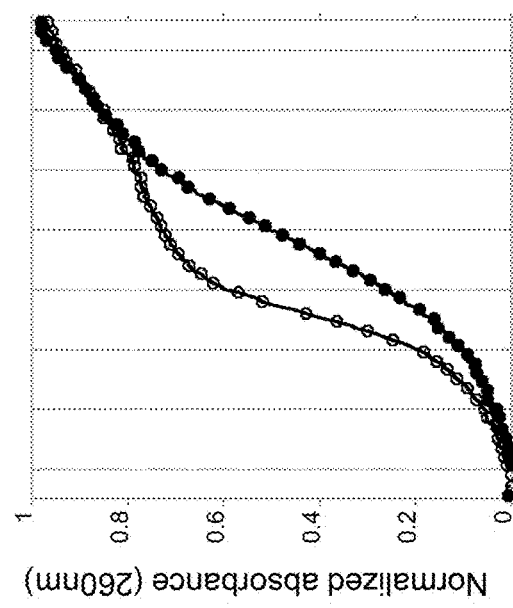

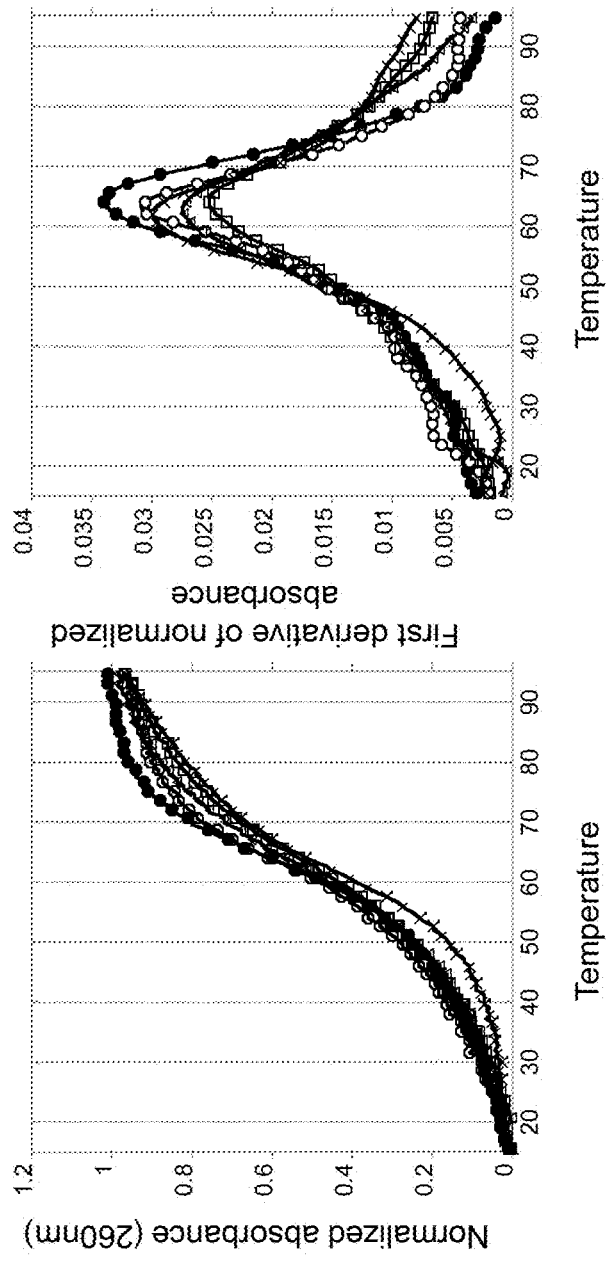
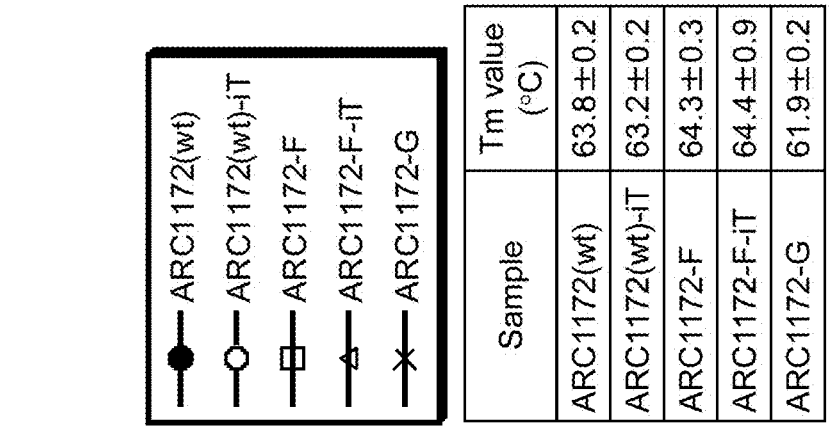
Fig. 20

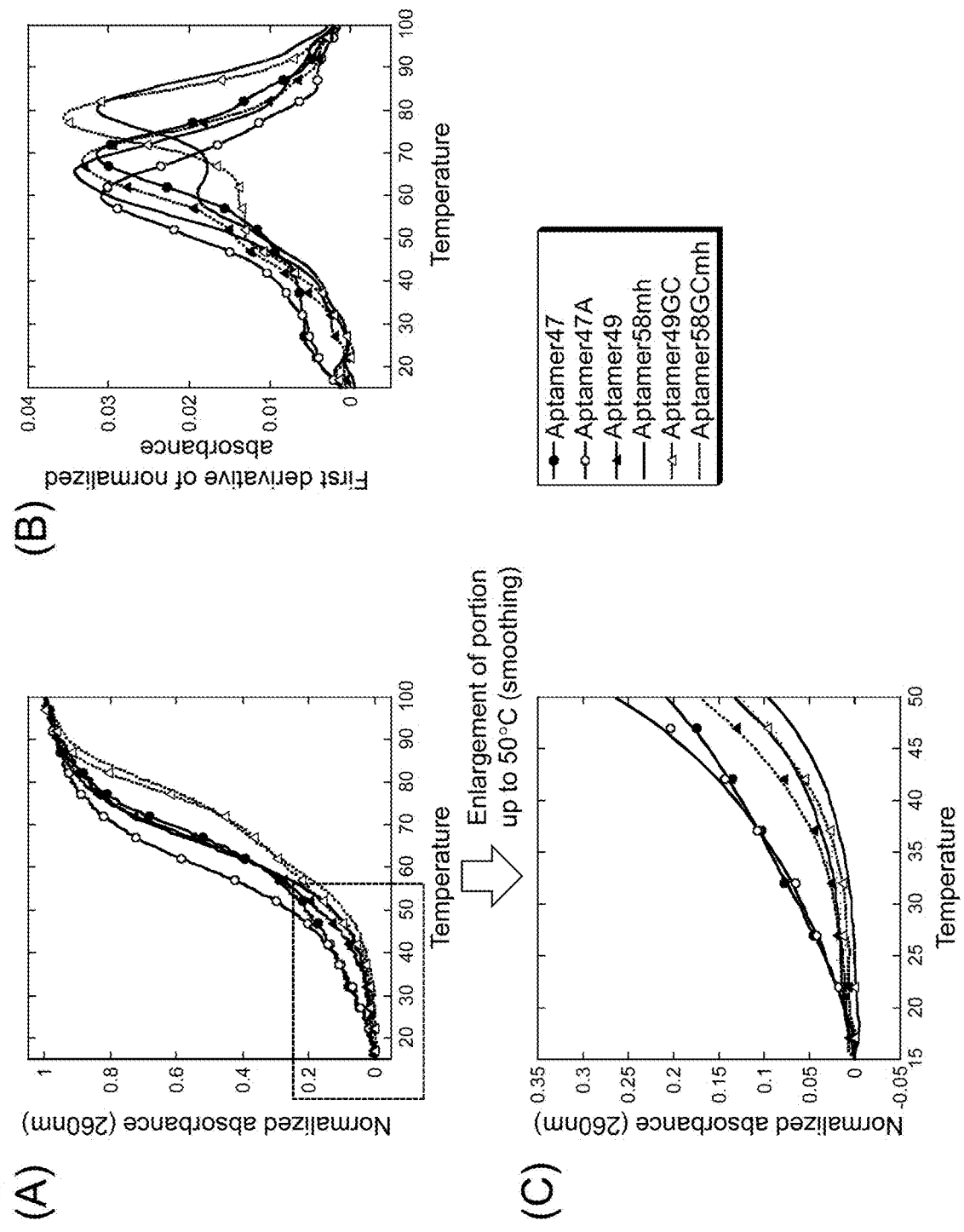

METHOD FOR STABILIZING DNA APTAMERS

CROSS-REFERENCE TO RELATED APPLICATIONS

This application is a National Stage application of PCT/JP2016/056805, filed Mar. 4, 2016, which claims priority from Japanese application JP 2015-045266, filed Mar. 6, 2015.

The instant application contains a Sequence Listing which has been submitted in ASCII format via EFS-WEB and is hereby incorporated by reference in its entirety. Said ASCII copy, created on Nov. 13, 2017, is named sequence.txt and is 8 KB.

TECHNICAL FIELD

The present mention relates to a method for designing a nucleotide sequence that enhances the capacity of a DNA aptamer to hind to a target molecule and/or stabilizes the DNA aptamer, and a DNA aptamer having such properties.

BACKGROUND ART

Functional nucleic acids, such as siRNAs, nucleic acid aptamers, and decoy nucleic acids, have drawn attention as pharmaceuticals or diagnostic agents in recent years, and research on and development of various nucleic acid drugs and the like are ongoing with the goal of establishing medical applications thereof all over the world.

The general problem of nucleic acids, however, is that these nucleic acids are likely to be degraded by nucleolytic enzymes, such as nucleases, in vivo. In vivo stabilization of the nucleic acids is essential problem for nucleic acid drugs to exert the pharmacological effects efficiently and continuously.

For improving the stability of nucleic acid aptamers against nucleolytic enzymes, a general approach involves chemically modifying sugar or phosphate portions, which are the backbones of nucleic acid, molecules (Non Patent Literatures 1 and 2 and Patent Literature 1). The problems of these modifications, however, are that the modifications might also influence the higher-order structure or physical properties of the nucleic acids; and the modifications might not only cause reduction in the capacity to bind to a target molecule or higher in vivo toxicity but increase production cost. Accordingly, under the present circumstances, it requires to modify modifiable sites, exhaustively screen them, and individually analyze them in order to practically use chemically modified nucleic acid aptamers as pharmaceuticals. Also, it is generally difficult to improve the capacity to bind to a target molecule by such chemical modifications, and there have been few reports thereon.

Thus, a convenient and low-cost method for enhancing the stability of a nucleic acid aptamer and further improving its capacity to bind to a target molecule has been demanded.

CITATION LIST

Patent Literature

Patent Literature 1: European Patent Application Publication No. 1931694

Non Patent Literature

Non Patent Literature 1: Peng, C. G., Masad, J., Damha, M. J., G-quadruplex induced stabilization by 2'-deoxy-2'-fluoro-D-arabinonucleic acids (2'F-ANA), 2007, Nucl. Acids Res., 35, pp. 4977-4988.

Non Patent Literature 2: Wang, R. E., Wu, H., Niu, Y., Cai, J., Improving the stability of aptamers by chemical modification, 2011, Curr. Med. Chem., pp. 4126-4138.

SUMMARY OF INVENTION

Technical Problem

An object of the present invention is to provide a convenient and low-cost method for enhancing the stability of a DNA aptamer and/or its capacity to bind to a target molecule, and a DNA aptamer obtained by the method.

Solution to Problem

The present inventors have completed the present invention by finding that the stability of an existing DNA aptamer and/or its capacity to bind to a target molecule can be enhanced by substituting an internal hairpin structure of the DNA aptamer with a structure called mini-hairpin structure and further optionally substituting A-T base pairs in a stem structure of the DNA, aptamer with G-C base pairs.

Thus, the present invention encompasses the following aspects:

(1) A method for designing a base sequence that enhances the capacity of an existing DNA aptamer to bind to a target molecule and/or stabilizes the aptamer, comprising substituting a hairpin structure consisting of one pair of stem structure and loop structure of the DNA aptamer comprising at least one stem structure and at least one loop structure with a mini-hairpin structure, wherein the mini-hairpin structure comprises: nucleic acid regions (A) to (C) below sequentially ligated from the 5' end toward the 3' end: (A) a first nucleic acid region comprising 2 to 5 arbitrary nucleotides; (B) a second nucleic acid region comprising a "gna" or "gnna" base sequence wherein each "n" independently represents either "g", "t", "a", or "c", a base analogue, or a modified base; and (C) a third nucleic acid region comprising a base sequence complementary to the first nucleic acid region, wherein the first nucleic acid region and the third nucleic acid region form a stem portion by base pairing with each other and the second nucleic acid region forms a loop portion.

(2) The method according to the above (1), wherein the DNA aptamer comprises at least one base analogue and/or modified base.

(3) The method according to the above (2), wherein the base analogue is 7-(2-thienyl)-3H-imidazo[4,5-b]pyridin-3-yl.

(4) The method according to any one of the above (1) to (3), comprising increasing one or more GC pails in stem structure other than that constituting the mini-hairpin.

(5) The method according to any one of the above (1) to (4), comprising increasing one to five GC pairs in the end of the DNA aptamer, when one of the at least one stem structure constitutes the end of the DNA aptamer.

(6) The method according to any one of the above (1) to (5), comprising adding the mini-hairpin structure defined in claim 1 to one end of the DNA aptamer.

(7) A method for producing a DNA aptamer being stabilized and/or having enhanced capacity to bind to a target molecule, comprising the steps of: designing a base sequence of a DNA aptamer in accordance with the method according to any one of the above (1) to (6); and producing a DNA aptamer on the basis of the designed base sequence.

(8) A DNA aptamer being stabilized and/or having enhanced capacity to bind to a target molecule, obtained by a production method comprising the steps of designing a base sequence of a DNA aptamer and producing a DNA aptamer on the basis of the designed base sequence, wherein the step of designing comprises substituting a hairpin structure consisting of one pair of stem structure and loop structure of an existing DNA aptamer comprising at least one stem structure and at least one loop structure with a mini-hairpin structure, and wherein the mini-hairpin structure comprises: nucleic acid regions (A) to (C) below sequentially ligated from the 5' end toward the 3' end: (A) a first nucleic acid region comprising 2 to 5 arbitrary nucleotides; (B) a second nucleic acid region comprising a "gna" or "gnna" base sequence wherein each "n" independently represents either "g", "t", "a", "c", a base analogue, or a modified base; and (C) a third nucleic acid region comprising a base sequence complementary to the first nucleic acid region, wherein the first nucleic acid region and the third nucleic acid region form a stem portion by base pairing with each other and the second nucleic acid region forms a loop portion.

(9) The DNA aptamer according to the above (8), comprising at least one base analogue and/or modified base.

(10) The DNA aptamer according to the above (9), wherein the base analogue is 7-(2-thienyl)-3H-imidazo[4,5-b]pyridin-3-yl.

(11) The DNA aptamer according to any one of the above (8) to (10), wherein the step of designing comprising increasing one or more GC pairs in stem structure other than that constituting the mini-hairpin.

(12) The DNA aptamer according to any one of the above (8) to (11), wherein the step of designing comprises increasing one to five GC pairs in the end of the DNA aptamer, when one of the at least one stem structure constitutes the end of the DNA aptamer.

(13) The DNA aptamer according to any one of the above (8) to (12), wherein the step of designing comprises adding the mini-hairpin structure defined in the above (8), to one end of the DNA aptamer.

(14) A DNA aptamer comprising at least one stem structure and at least one loop structure, wherein at least one hairpin structure located in a region other than the end of the DNA aptamer and consisting of one pair of stem structure and loop structure comprises: nucleic acid regions (A) to (C) below sequentially ligated from the 5' end toward the 3' end: (A) a first nucleic acid region comprising 2 to 5 arbitrary nucleotides; (B) a second nucleic acid region comprising a "gna" or "gnna" base sequence wherein each "n" independently represents either "g", "t", "a", or "c", a base analogue, or a modified base; and (C) a third nucleic acid region comprising a base sequence complementary to the first nucleic acid region, wherein the first nucleic acid region and the third nucleic acid region form a stem portion by base pairing with each other and the second nucleic acid region forms a loop portion.

(15) The DNA apt-tinier according to the above (14), wherein the total GC content in the at least one stem structure is at least 75%.

(16) The DNA aptamer according the above (14) or (15), further comprising the hairpin structure defined in the above (14) at one end.

(17) A DNA aptamer for IFN-γ consisting of the nucleotide sequence as shown in any of SEQ ID NOs: 6 and 8 to 11.

(18) A DNA aptamer for VEGF consisting of the nucleotide sequence as shown in any of SEQ ID NOs: 19 to 22.

(19) A DNA aptamer for vWF consisting of the nucleotide sequence as shown in any of SEQ ID NOs: 14 to 16.

(20) A pharmaceutical composition comprising the DNA aptamer according to any one of the above (8) to (19).

The present invention encompasses the disclosure of JP Patent application No. 2015-045266, to which the present application claims priority.

According to the method of the present invention, a low-cost and convenient preparation method can stabilize a DNA aptamer, allow the DNA aptamer to secure high stability in vivo, and/or enhance its capacity to bind to a target molecule. As a result, the DNA aptamer can continuously exert its pharmacological effect over a long period of time.

BRIEF DESCRIPTION OF DRAWINGS

FIG. 1 shows one example of the step 1 of the present invention. FIG. 1(A) shows an example of substituting a hairpin structure with a mini-hairpin structure. FIG. 1(B) shows an example of substituting a hairpin structure comprising one bulge structure in the stem structure with a mini-hairpin structure. FIG. 1(C) shows an example of substituting a hairpin structure comprising one internal loop structure in the stem structure with a mini-hairpin structure. In the diagram, reference numeral 101 denotes a stem structure, reference numeral 102 denotes a loop structure, reference numeral 103 denotes a hairpin structure, reference numeral 104 denotes a first nucleic acid region, reference numeral 105 denotes a second nucleic acid region, reference numeral 106 denotes a third nucleic acid region, reference numeral 107 denotes a mini-hairpin structure, reference numeral 108 denotes a bulge structure, and reference numeral 109 denotes an internal loop structure.

FIG. 2 shows one example of the step 2 of the present invention. FIG. 2(A) shows an example of adding the same number of bases as that of bases constituting a bulge structure to the other strand. FIG. 2(B) shows an example of adding a smaller number of bases than that of bases constituting a bulge structure to the other strand. In the diagram, reference character S denotes G or C, and reference character S' denotes a complementary base of S.

FIG. 4(A) shows an example of substituting all of bases constituting an internal loop with GC pairs. FIG. 4(B) shows an example of substituting a portion of the bases with GC pairs, wherein this substitution occurs at the end of the internal loop structure. FIG. 4(C) shows an example of substituting a portion of the bases with GC pairs, wherein this substitution occurs within the internal loop structure. In the diagram, reference character N denotes A, T, G, or C, reference character S denotes G or C, and reference character S' denotes a complementary base of S.

In FIG. 10(A), the abscissa shows temperature, and the ordinate shows normalized absorbance. In FIG. 10(B), the abscissa shows temperature, and the ordinate shows a first derivative of the normalized absorbance.

FIG. 11 is a diagram showing results of measuring the inhibitory effect of each aptamer for IFN-γ on response to IFN-γ stimulation by FACS using cultured cells. FIG. 11(A) is a schematic diagram showing that STAT1 is phosphorylated by IFN-γ stimulation. FIG. 11(B) shows results of FACS analysis using a phosphorylated STAT antibody. The abscissa shows fluorescence intensity. The ordinate shows the number of cells. Unstimulated cells are indicated by an area filled with gray. Unstimulated cells that were not treated with an anti-phosphorylated STAT-1 antibody solution are indicated by a line. FIG. 11(C) shows FACS analysis on IFN-γ treated cells using a phosphorylated STAT antibody. The abscissa shows fluorescence intensity. The ordinate shows the number of cells. Unstimulated cells are indicated by an area filled with gray. Cells stimulated with IFN-γ are indicated by a line.

FIG. 16 is a diagram showing results of measuring the Tm value of each aptamer for IFN-γ consisting of natural bases. In the graph of FIG. 16(A), the abscissa shows temperature, and the ordinate shows normalized absorbance. In the graph of FIG. 16(B), the abscissa shows temperature, and the ordinate shows a first derivative of the normalized absorbance.

FIG. 20 is a diagram showing results of measuring the Tm value of each aptamer for vWF A1 domain. In the graph of FIG. 20(A), the abscissa shows temperature, and the ordinate shows normalized absorbance. In the graph of FIG. 20(B), the abscissa shows temperature, and the ordinate shows a first derivative of the normalized absorbance.

FIG. 24 is a diagram showing results of measuring the Tm value of each aptamer for VEGF165. In the graph of FIG. 24(A), the abscissa shows temperature, and the ordinate shows normalized absorbance. In the graph of FIG. 24(B), the abscissa shows temperature, and the ordinate shows a first derivative of the normalized absorbance. The graph of FIG. 24(C) is enlargement of a portion up to 50° C. of the graph of FIG. 24(A).

DESCRIPTION OF EMBODIMENTS

1. Definition

Figure 3:
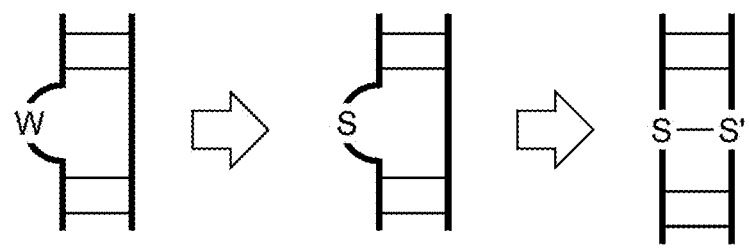
FIG. 3 shows one example of the step 2 of the present invention, wherein A or T in a bulge structure is substituted with G or C, and then, a complementary base of the substituted base is added. In the diagram, reference character W denotes A or T, reference character S denotes G or C, and reference character S' denotes a complementary base of S.

The general terms used in the present specification are defined as follows:

In the present specification, the "nucleic acid" or the "nucleic acid molecule" refers to a biological polymer that is constituted by nucleotide units linked through phosphodiester bonds, as a rule.

In the present specification, the "natural nucleotide" refers to a naturally occurring nucleotide. Examples thereof include DNAs composed of deoxyribonucleotides having any of the natural bases adenine, guanine, cytosine, and thymine, RNAs composed of ribonucleotides having any of the natural bases adenine, guanine, cytosine, and uracil, and combinations thereof. A nucleic acid (molecule) constituted only by natural nucleotides is referred to as a natural nucleic acid (molecule) in the present specification.

In the present specification, the "non-natural nucleotide" refers to a non-naturally occurring nucleotide constituted by an artificial base. A phosphate group and a sugar constituting the non-natural nucleotide according to the present invention are structurally identical to those of the natural nucleotide.

In the present specification, the "base analogue" or the "artificial base" refers to an artificially constructed chemical substance having properties similar to those of the natural base constituting the natural nucleotide and can form artificial base pairing with its partner base analogue (hereinafter, referred to as a "complementary artificial base" the present specification), as in the natural base. In the present specification, the "artificial base pairing" refers to base pairing formed between a pair of complementary artificial bases, as in a pair of complementary natural bases adenine and thymine, adenine and uracil, or guanine and cytosine. The artificial base pairing includes a chemical bond via a hydrogen bond found in the base pairing between natural bases, a physical bond via the molecular structure-based association between artificial bases, and stacking effects is hydrophobic interaction.

The "properties similar to those of the natural base" possessed by the artificial base include properties that permit nucleic acid replication or transcription (including reverse transcription) through the complementary of artificial base pairing. The artificial base has exclusive selectivity in artificial base pairing, as in the natural base. Thus, even a nucleic acid molecule comprising a non-natural nucleotide, as with the natural nucleotide, can be replicated or transcribed accurately through the complementary between artificial bases, if non-natural nucleotides respectively having a pair of complementary artificial bases are present among substrate nucleotides. This allows, for example, a DNA molecule to be amplified by a nucleic acid amplification method such as PCR, while the molecule comprises a non-natural nucleotide.

Specific examples of the artificial base include Ds (7-(2-thienyl)imidazo[4,5-b]pyridine; referred to as "Ds" in the present specification), Pn (2-nitropyrrole-1-yl; referred to as "Pn" in the present specification), Pa (2-formyl-1H-pyrrole-1-yl; referred to as "Pa" in the present specification), P (2-amino-imidazo[1,2-a]-1,3,5-triazin-4(8H)-one; referred to as "P" in the present specification), Z (6-amino-5-nitro-2(1H)-pyridone; referred to as "Z" in the present specification), 5SICS (6-methylisoquinoline-1(2H)-thione; referred to as "5SICS" in the present specification), NaM (3-methoxynaphthalen-2-yl; referred to as "NaM" in the present specification), and MMO2 (2-methoxy-4-methylphenyl; referred to as "MMO2" in the present specification). Examples of the complementary artificial base of the artificial base Ds include Pn and Pa. Examples of the complementary artificial base of P include Z. Examples of the complementary artificial base of 5SICS include NaM and MMO2.

In the absence of a non-natural nucleotide having a complementary artificial base in substrates, the artificial base can instead pair with a natural base similar in structure and/or properties to the complementary artificial base during replication or transcription. In this case, the non-natural nucleotide in the templated nucleic acid molecule is replaced with a natural nucleotide after replication or transcription. For example, Ds is known to be replaced with A or T.

In the present specification, the "modified base" means an artificially chemically modified base. Examples of the modified base include modified pyrimidine (e.g., 5-hydroxycytosine, 5-fluorouracil, 4-thiouracil, 5-(3-indole-2-ethyl)uracil, and 5-(4-hydroxyphenyl-2-ethyl)uracil), modified purine (e.g., 6-methyladenine and 6-thioguanosine), and other heterocyclic bases.

In the present specification, the "nucleic acid aptamer" refers to an aptamer constituted by a nucleic acid and refers to a ligand molecule that is able to strongly and specifically bind to a target molecule through the secondary structure of a single-stranded nucleic acid molecule and further the conformation formed on the basis of a tertiary structure via a hydrogen bond or the like, thereby specifically inhibiting or suppressing the functions (e.g., biological activity) of the target molecule. Thus, the nucleic acid aptamer can serve as an inhibitor of a target molecule function. In the present specification, the "functional inhibition of a target molecule" refers to inhibition or suppression of the catalytic function or gene expression control function (including control of transcription, translation, transport, etc.) and/or biological function such as apoptosis control function of the target molecule.

The nucleic acid aptamer is generally known as RNA aptamers consisting of RNAs and DNA aptamers consisting of DNAs. In the present specification, nucleic acids constituting a nucleic acid aptamer are DNA.

In the present specification, the "target molecule" refers to a substance that can serve as a target to which the DNA aptamer binds. The type of the target molecule is not particularly limited as long as the target molecule is a biomaterial to which the DNA aptamer can bind. Examples thereof include peptides (oligopeptides and polypeptides), nucleic acids, lipids, sugars (including sugar chains), and low-molecular-weight compounds. The target molecule is preferably a peptide, more preferably a polypeptide, i.e., a protein. Alternatively, the target molecule may be any of naturally derived substances, chemically synthesized substances, recombinant substances, cells, viruses, and the like.

2. Method for Designing DNA Aptamer

According to the first embodiment, the present invention relates to a method for designing a nucleotide sequence that enhances the capacity of an existing DNA aptamer to bind to a target molecule and/or stabilizes the aptamer. The present invention particularly relates to a method capable of enhancing the capacity of a DNA aptamer to bind to a target molecule and/or stabilizing the aptamer on the basis of information at the secondary structure level of the DNA aptamer. The method for designing a nucleotide sequence according to the present invention comprises step 1 as an essential step. Also, the method for designing a nucleotide sequence according to the present invention comprises one or more of step 2, step 3, and step 4 as optional steps. When the method of the present in comprises these optional steps, the order of the steps is not limited. However, when the method of the present invention comprises both of step 3 and step 4, the step 4 is carried out after the step 3. Each step constituting the method for designing a nucleotide sequence according to the present invention will be described below.

2-1. Step 1

In the present specification, the "step 1" is the step of substituting a hairpin structure consisting of one pair of stem structure and loop structure of the existing DNA aptamer comprising at least one stem structure and at least one loop structure with a mini-hairpin structure.

In the present specification, the "stem structure" means a double-stranded structure formed by the complete or partial base pairing of a portion of bases, preferably 2 or more consecutive, for example 3 or more, 4 or more, or 5 or more consecutive bases constituting one strand with bases constituting another strand. In the present specification, the "complete" base pairing means that all of 2 or more consecutive, for example, 3 or more, 4 or more, or 5 or more consecutive bases in one nucleotide sequence of a DNA aptamer are base-paired with the corresponding bases of another nucleotide sequence. The "partial" base pairing means that 1 or 2 or more, for example, 3 or more 4 or more, or 5 or more unpaired bases are contained in the completely base-paired nucleotide sequences of the stem structure. Thus, in this case, at least one internal loop structure and/or at least one bulge structure is formed within the stem structure. In the present specification, the "internal loop structure" refers to a loop structure that is formed within the stem structure, when at least one unpaired base is present at each of the corresponding positions of two strands constituting the stem structure. In the present specification, the "bulge structure" refers to a protruding structure that is formed within the stem structure, when at least one unpaired base is present at either of the corresponding positions of two strands constituting the stem structure.

In the present specification, the "loop structure" means an unpaired loop-shaped structure that is positioned in two strands constituting the stem structure and formed within the nucleic acid by the formation of the stem structure.

In the present specification, the "hairpin structure" or the "stem-loop structure" means a structure consisting of one stem structure and one loop structure (one pair of stem structure and loop structure).

In the present specification, the "mini-hairpin structure" has a structure where three DNA nucleic acid regions, i.e., a first nucleic acid region, a second nucleic acid region, and a third nucleic acid region, are sequentially ligated from the 5' end toward the 3' end.

The "first nucleic acid region" is a nucleic acid region comprising 2 to 5 arbitrary nucleotides. The nucleotides refer to deoxyribonucleotides having a base guanine (g), adenine (a), cytosine (c), or thymine (t). The base of this nucleic acid region is preferably guanine or cytosine. This is because, for forming a stem structure with the third nucleic acid region mentioned later, a larger gc content elevates a Tm value and allows the stem structure to be stably retained. Thus, the whole nucleotide sequence of the first nucleic acid region most preferably consists of g and/or c.

The "second nucleic acid region" is a nucleic acid region comprising a 5'-gna-3' or 5'-gnna-3' nucleotide sequence. In the sequence, each n independently represents a natural base (g, a, t, or c), the base analogue, or the modified base.

The "third nucleic acid region" is a nucleic acid region having a nucleotide sequence complementary to that of the first nucleic acid region. Thus, the nucleotide sequence of the third nucleic acid region is determined by the nucleotide sequence of the first nucleic acid region. Also, the first nucleic acid region and the third nucleic acid region are based-paired with each other within the molecule. As a result, the first nucleic acid region and the third nucleic acid region form a stem portion by complete base pairing with each other, and the second nucleic acid region between the first nucleic acid region and the third nucleic acid region forms a loop portion. For example, 7 to 14 nucleotide mini-hairpin DNA having the nucleotide sequence of SEQ ID NO: 1, 2, 23, or 24 is formed as a whole.

A DNA aptamer of interest of the step 1 is an existing DNA aptamer comprising at least one stem structure and at least one loop structure. In the present specification, the "existing DNA aptamer" is a known DNA aptamer or a DNA aptamer obtained by a method known in the art whose nucleotide sequence has been revealed or can be revealed. In the case of preparing a DNA aptamer, the DNA aptamer can be prepared by, for example, in vitro selection using a modified version of known SELEX (systematic evolution of ligands by exponential enrichment). The SELEX method involves selecting nucleic acid molecules bound to a target molecule from an pool composed of nucleic acid molecules having random sequence regions and primer-binding regions at both ends thereof, amplifying the nucleic acid molecules after recovery, and then using the molecules as a nucleic acid pool for the subsequent round. This series of cycles is repeated at several to several tens of rounds to select nucleic acid(s) having higher binding strength against the target molecule. The modified version of SELEX involves, in addition to these steps of the conventional SELEX method, the step of immobilizing a complex obtained by the mixing of a nucleic acid pool with a target molecule onto a solid-phase carrier. For the details of the modified version of SELEX, see WO2013/073602. The DNA molecule finally obtained by such a method can be used as the DNA aptamer.

Those skilled in the art can readily identify a nucleotide sequence constituting the stem structure and the loop structure in the DNA aptamer by predicting a secondary structure on the basis of the nucleotide sequence thereof. For the prediction of a secondary structure on the basis of the nucleotide sequence, of the nucleic acid, see for example, Zuker M., "Mfold web server for nucleic acid folding and hybridization prediction", Nucleic Acids Res. 2003, 31, pp. 3406-3415.

Alternatively, the secondary structure is, predicted by preparing a library of mutagenized nucleotide sequences of a DNA aptamer (doped library), using it in SELEX, exhaustively analyzing sequences binding to a target, and determining a site at which base pairs are conserved (see e.g., Kimoto M., et al., "Generation of high-affinity DNA aptamer using an expanded genetic alphabet" Nat. Biotechnol., 2013, 31, pp. 453-457). For the existing DNA aptamer, the secondary structure of the DNA aptamer can also be predicted by use of structure information thereon obtained by X-ray crystallography or NMR.

The base length of the existing DNA aptamer is not particularly limited. The base length can be appropriately set within the range where the DNA aptamer can exert its capacity to bind to a target.

The existing DNA aptamer may comprise at least one base analogue and/or modified base. The content of the base analogue and/or modified base in the DNA aptamer of the present invention may be 20% or less, preferably 15% or less, more preferably 10% or less, of the total number of nucleotides constituting the nucleic acid aptamer.

The hairpin structure to be substituted in this step preferably has a size equivalent to that of the mini-hairpin structure after the substitution. In this context, the "equivalent size" means that the difference in nucleotide length between the hairpin structure to be substituted and the mini-hairpin structure after the substitution is preferably 5 or less, for example, 4 or less, 3 or less, 2 or less, or 1 or less, or the hairpin structure to be substituted and the mini-hairpin structure after the substitution have the same nucleotide length. Since the mini-hairpin structure consists of 7 to 14 bases as described above the hairpin structure to be substituted preferably consists of, for example, 7 to 19 bases.

The stem structure constituting the hairpin structure to be substituted in this step may have one to three internal loop structures and/or one to three bulge structures. In this context, the number of bases constituting each internal loop structure in the stem structure is, for example, 10 or less, preferably 6 or less, 5 or less, 4 or less, 3 or less, or 2, in the total of the two strands. The number of bases constituting each bulge saliently in the stem structure is, for example, 10 or less, preferably 6 or less, 5 or less, 4 or less, 3 or less, 2 or less, or 1.

As examples of this step, the substitutions of hairpin structures comprising a stem structure comprising neither internal loop structure nor bulge structure, a stem structure comprising one internal loop structure, or a stem structure comprising one bulge structure with a man-hairpin structure are shown in FIGS. 1(A), 1(B), and 1(C), respectively.

The substitution of the hairpin structure with the mini-hairpin structure may be carried out by partially changing the nucleotide sequence constituting the hairpin structure or by completely changing the nucleotide sequence constituting the hairpin structure.

When two or more hairpin structures are present in the existing DNA aptamer, these two or more hairpin structures may each be substituted with a mini-hairpin structure. For example, the whole hairpin structures can be substituted therewith.

The hairpin structure to be substituted in this step is preferably a hairpin structure that is not involved in the binding of the DNA aptamer to the target molecule or makes a small contribution to the binding thereof to the target molecule. Those skilled in the art can readily identify the hairpin structure that is not involved in the binding of the DNA aptamer to the target molecule or makes a small contribution to the binding thereof to the target molecule, for example, by conducting X-ray crystallography or NMR analysis on a complex of the DNA aptamer and the target molecule. In the case of a DNA aptamer obtained by a screening method such as the modified version of SELEX, the hairpin structure that is not involved in the binding to the target molecule or makes a small contribution to the binding to the target molecule can also be predicted from a sequence conserved among selected DNA aptamers. For example, the hairpin structure that is not involved in the binding to the target molecule or makes a small contribution to the binding to the target molecule can be predicted by preparing a library of mutagenized nucleotide sequences of a DNA aptamer (doped library), using it in SELEX, exhaustively analyzing sequences binding to a target, and determining a site at which base pairs are conserved.

2-2. Step 2

In the present specification, the "step 2" is the step of increasing GC pairs in at least one stem structure, when the existing DNA aptamer has two or more stem structures. This step can be carried out by substituting one or more AT pairs in the stem structure with GC pairs and/or adding GC pairs into the stem structure. The site of the stem structure of interest of the step 2 is not particularly limited as long as this site is not contained in the stem structure constituting the mini-hairpin structure. The number of GC pairs to be increased is, for example, 10 pairs or less, preferably 5 pairs or less, 4 pairs or less, 3 pairs or less, 2 pairs or less, or 1 pair. For example, in the case of the substitution, all of AT pairs in the stem structure may be substituted with GC pairs, or, for example, 10 pairs or less, preferably 5 pairs or less, 4 pairs or less, 3 pairs or less, 2 pairs or less, or 1 pair, of the AT pairs in the stem structure may be substituted with GC pairs. Likewise, in the case of adding GC pairs into the stem structure, for example, 10 pairs or less, preferably 5 pairs or less, 4 pairs or less, 3 pairs or less, 2 pairs or less, or 1 pair, of the GC pairs may be added into the stem structure. The site to which GC pairs are added may be the end of the stem structure or may be an internal region of the stem structure.

When the DNA aptamer comprises a bulge structure or an internal loop structure in the stem structure, in addition to or instead of substituting one or more AT pairs in the stem structure with GC pairs and/or adding GC pairs into the stem structure, GC pairs in the stem structure may be increased by subjecting bases constituting the bulge structure or the internal loop structure to such substitution and/or addition. Hereinafter, 4 separate cases will be described: (i) the case where the bulge structure comprises a base G or C, (ii) the case where the bulge structure comprises, a base A or T, (iii) the case where the number of nucleotides constituting the internal loop structure is equal between one strand and another strand, and (iv) the case where the number of nucleotides constituting the internal loop structure differs between one strand and another strand.

(i) Case where Bulge Structure Comprises Base G or C

In this case, GC pairs in the stem structure may be increased by adding G or C to the other strand so that that added base(s) are base-paired with base(s) constituting the bulge structure. The same number of bases as that of bases constituting the bulge structure may be added to the other strand. In this case, after the base addition, bases of the two strands constituting the stem structure are completely paired so that the bulge structure no longer exists. A smaller number of bases than that of bases constituting the bulge structure may be added to the other strand. In this case, after the base addition, bases of the two strands constituting the stem structure are partially paired so that the bulge structure remains. The number of G or C to be added is not particularly limited as long as a smaller number of G or C than that of bases constituting the bulge structure is added. The number of G or C to be added is, for example, 10 less, preferably 5 or less, 4 or less, 3 or less, 2 or less, or 1 or less.

One example of adding the same number of bases as that of bases constituting the bulge structure to the other strand and one example of adding a smaller number of bases than that of bases constituting the bulge structure to the other strand are shown in FIGS. 2(A) and 2(B), respectively.

(ii) Case where Bulge Structure Comprises Base A or T

In this case, GC pairs in the stem structure may be increased by substituting A or T constituting the bulge structure with G or C, and then adding G or C to the other strand so that that added base(s) are base-paired with the substituted base(s). After the substitution of A or T constituting the bulge structure with G or C, G or C is added in accordance with the case (i). All of bases A or T constituting the bulge structure may be subjected to such substitution and addition, or a portion of the bases A or T may be subjected to the substitute and addition.

One example of this step is shown in FIG. 3.

(iii) Case where the Number of Nucleotides Constituting Internal Loop Structure is Equal Between One Strand and Another Strand In this case, GC pairs in the stem structure may be increased by substituting the same numbers of bases, for example, 10 bases or less, preferably 5 bases or less, 4 bases or less, 3 bases or less, 2 bases or less, or 1 base each, of the two strands constituting the internal loop present in the stem structure with GC pairs. All of bases constituting the internal loop may be substituted with GC pairs, or a portion of the bases may be substituted with GC pairs. When a portion of the bases are substituted with GC pairs, this substitution with GC pairs preferably occurs at the end of the internal loop structure, i.e. the portion at which the internal loop is in contact with the stem structure. When this substitution with GC pairs occurs within the internal loop structure, i.e., a portion in the internal loop with which the stem structure is not in contact, an additional bulge structure and/or internal loop structure may be formed in the stem structure. In this case, the newly formed bulge structure and/or internal loop structure may be subjected to substitution and/or addition in accordance with the cases (i) to (iv) to further increase GC pairs in the stem structure.

Figure 4:
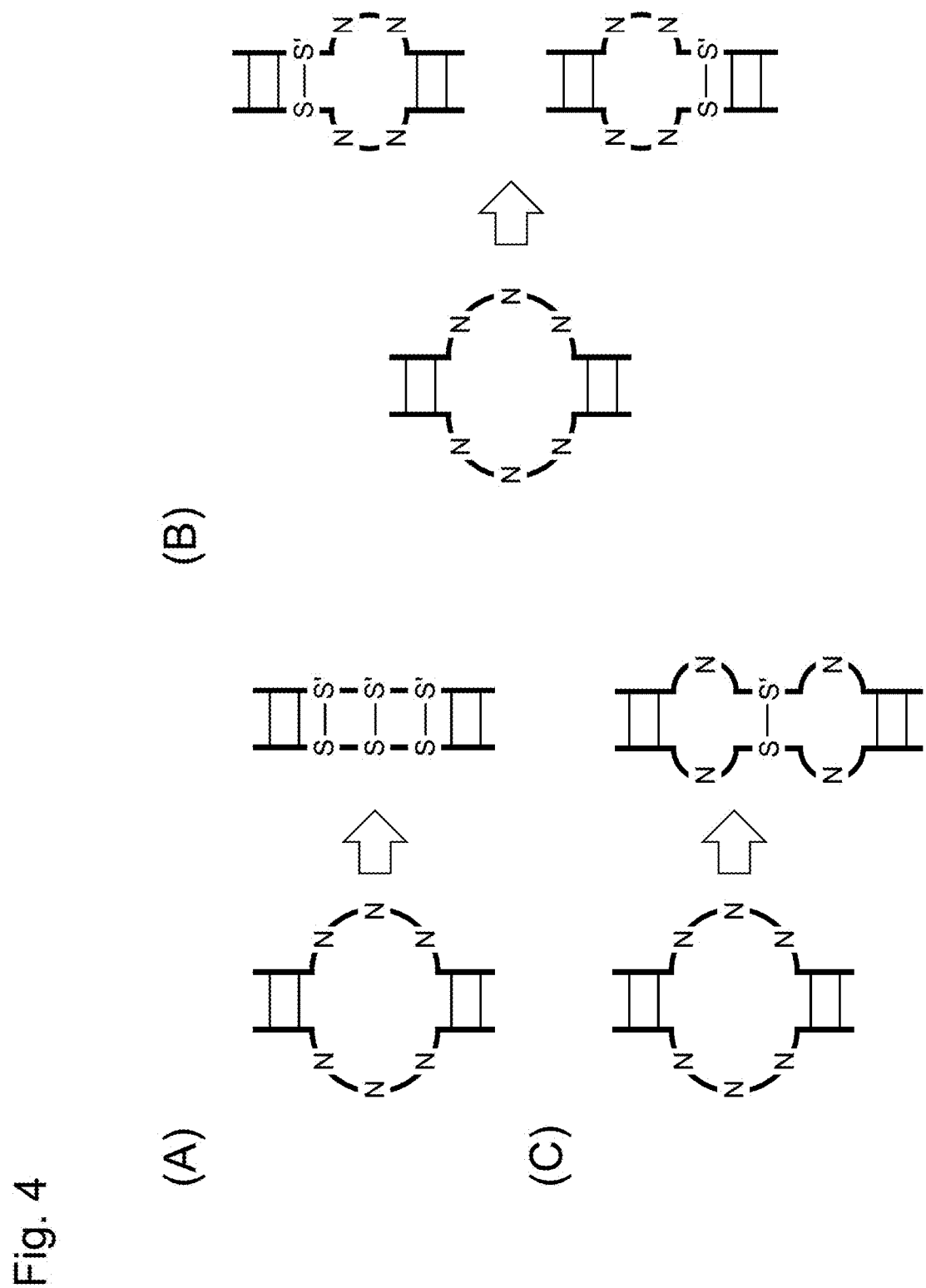
FIG. 4 shows one example of the step 2 of the present invention.

One example of substituting all of bases constituting the internal loop with GC pairs, one example of substituting a portion of the bases with GC pairs, wherein this substitution occurs at the end of the internal loop structure, and one example of substituting a portion of the bases with GC pairs, wherein this substitution occurs within the internal loop structure are shown in FIGS. 4(A), 4(B), and 4(C), respectively.

(iv) Case where the Number of Nucleotides Constituting Internal Loop Structure Differs Between One Strand and Another Strand As in the case (iii), GC pairs in the stem structure may be increased by substituting the same numbers of unpaired bases, for example, 10 unpaired bases or less, preferably 5 impaired bases or less, 4 unpaired bases or less, 3 unpaired bases or less, 2 unpaired bases or less, or 1 unpaired base each, of the two strands of the stem structure with GC pairs. The substitution site is the same as in the case (iii), so that the description is omitted. In the case (iv), however, a bulge structure is finally formed in the one strand by increasing the same numbers of substitutions of unpaired bases in the two strands with GC pairs. In this case, the formed structure may be subjected to substitution and/or addition in accordance with the case (i) or (ii) to further increase GC pairs in the stem structure.

Figure 5:
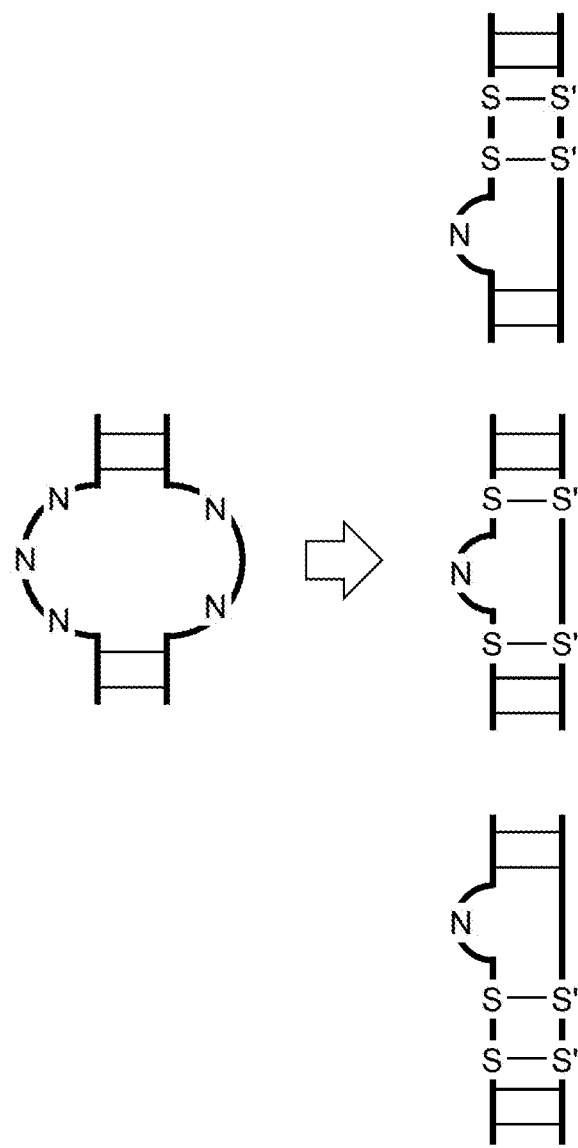
FIG. 5 shows one example of the step 2 of the present invention. This diagram shows that a bulge structure is finally formed in one strand, as the same numbers of substitutions with GC pairs are increased in two strands, when the number of nucleotides constituting an internal loop structure of one strand differs from that of another strand. In the diagram, reference character N denotes A, T, G, or C, reference character S denotes G or C, and reference character S' denotes a complementary base of S.

One example of this step is shown in FIG. 5.

2-3. Step 3

In the present specification, the "step 3" is the step of increasing GC pairs at the end of the DNA aptamer, when at least one end of the DNA aptamer forms a stem structure. The number of GC pairs to be added is not limited as long as the binding activity of the resulting DNA aptamer against the target molecule is not reduced. The number of GC pairs to be added is, for example, 5 pairs or less, preferably 3 pairs, or less, 2 pairs or less, 1 pair.

This step can be carried out by adding GC pair(s), i.e., G and C or C and G, to the 5' end and the 3' end, respectively. When one strand of the stem structure constituting the end of the DNA aptamer has a protruding end comprising base(s) G or C, this step can be carried out by adding G or C to the other strand so as to form base pairing with the base(s) constituting this protruding end. When one strand of the stem structure constituting the end of the DNA aptamer has a protruding end comprising base(s) A or T, this step can be carried out by substituting this base(s) with G or C and then adding G or C to the other strand so as to form base pairing with the base(s) constituting this protruding end.

2-4. Step 4

In the present specification, the "step 4" is the step of adding the mini-hairpin structure to one end of the DNA aptamer. Whether the mini-hairpin structure is added to the 5' end or the 3' end is not particularly limited. The mini-hairpin structure is preferably added to the 3' end.

2-5. Effect

The method for designing a nucleotide sequence according to the present invention can enhance the capacity of an existing DNA aptamer to bind to a target molecule and/or stabilize the aptamer.

In the present specification, the "capacity to bind to a target molecule" means the ability to bind to a target molecule. An enhanced capacity to bind to a target molecule can improve the ability of the DNA aptamer to specifically inhibit or suppress the functions (e.g., biological activity) of the target molecule.

In the present specification, the "stabilization" means increase in stability against heat and/or increase in stability against nucleolytic enzymes. An enhanced stability against heat and stability against nucleolytic enzymes can enhance in vivo stability.

3. Method for Producing a DNA Aptamer Being Stabilized and/or Having Enhanced Capacity to Bind to Target Molecule According to the second embodiment, the present invention relates to a method for producing a DNA aptamer being stabilized and/or having enhanced capacity to bind to a target molecule, comprising the steps of: designing a nucleotide sequence of a DNA aptamer in accordance with the method for designing a nucleotide sequence according to the first embodiment; and producing the DNA aptamer on the basis of the designed nucleotide sequence. The step of designing is as described in the first embodiment, so that the description is omitted here.

In the present specification, the "DNA aptamer being stabilized and/or having enhanced capacity to bind to a target molecule" means a DNA aptamer that has stronger capacity to bind to a target molecule and/or is more stabilized than the existing DNA aptamer used in the method for designing a nucleotide sequence according to the first embodiment.

The step of producing a DNA aptamer is not particularly limited. A method known in the art may be used. For example, the DNA aptamer of the present invention may be chemically synthesized in accordance with a known solid-phase synthesis method on the basis of the designed sequence of the DNA aptamer as described above. For the chemical nucleic acid synthesis method, see, for example, Current Protocols in Nucleic Acid Chemistry, Volume 1, Section 3. As for such chemical synthesis, many life science manufacturers (e.g., Takara Bio Inc., Life Technologies Corporation, and Sigma-Aldrich Corporation) provide contract manufacturing services, and these services may be used. Several fragments may be synthesized on the basis of the designed sequence of the DNA aptamer and then linked by intramolecular annealing or ligation or the like using ligase to prepare the DNA aptamer.

The DNA aptamer of the present invention thus chemically synthesized is preferably purified by a method known in the art before use. Examples of the purification method include gel purification, affinity column purification, HPLC methods, and the like.

4. DNA Aptamer

According to the third embodiment, the present invention relates to a DNA aptamer comprising at least one stem structure and loop structure, wherein a hairpin structure located in a region other than the end of the DNA aptamer is the mini-hairpin structure. The DNA aptamer of the present invention may be obtained by the production method described in the second embodiment.

In the present specification, the "region other than the end" is not particularly limited as long as the region is any region of the DNA aptamer except for the 5' end and the 3' end. The region other than the end of the DNA aptamer is, for example, a site preferably 2 bases or more, for example, 3 bases, 4 bases, or 5 bases or more, distant from the end portion of the DNA.

The DNA aptamer of the present invention may further comprise the mini-hairpin structure at one end, in addition to the mini-hairpin structure in the region other than the end. Whether the DNA aptamer comprises the mini-hairpin structure at 3' end or 5' end is not limited. Particularly preferably, the DNA aptamer comprises the mini-hairpin structure at the 3' end. The DNA aptamer of the present invention may further have at least one stem structure and/or at least one loop structure, in addition to the mini-hairpin structure. In this case, the stem structure of the DNA aptamer may internally have at least one base mismatch site or at least one bulge structure.

The base length of the DNA aptamer of die present invention is not particularly limited. The base length can be appropriately set within the range where the DNA aptamer can exert its functions.

The DNA aptamer of the present invention may comprise at least one base analogue and/or modified base. The content of the base analogue and/or modified base in the DNA aptamer of the present invention may be 20% or less, preferably 15% or less, more preferably 10% or less, of the total number of nucleotides constituting the nucleic acid aptamer.

The DNA aptamer of the present invention preferably has a high GC content in at least one, for example, one, two, three, or all stem structures. The GC content means the ratio of GC pairs to all base pairs constituting stem structures contained in the DNA aptamer. The GC content in at least one, for example, one, two, three, or an stem structures of the DNA aptamer of the present invention is, for example, 50% or more, 75% or more, or 90% or more. All base pairs in at least one, for example, one, two, three, or all stem structures may be GC pairs. When the end of the DNA aptamer of the present invention has a stem structure, the terminal base pair is preferably a GC pair.

5. DNA Aptamer for IFN-γ

The fourth embodiment of the present invention relates to a DNA aptamer for interferon-γ (abbreviated to "IFN-γ" in the present specification). The DNA aptamer for IFN-γ of the present invention has the constitution of the DNA aptamer described in the third embodiment.

The DNA aptamer for IFN-γ of the present invention is a DNA aptamer comprising a single-stranded DNA molecule that strongly and specifically binds to IFN-γ as a target substance and inhibits the cytotoxic T cell-inducing activity of IFN-γ (hereinafter, this DNA aptamer is referred to as a "DNA aptamer for IFN-γ"). The organism species from which the target molecule IFN-γ of the DNA aptamer for IFN-γ of the present invention is derived is not limited. Examples thereof include IFN-γ from mammals, for example, primates such as humans and chimpanzee, laboratory animals such as rats and mice, livestock animals such as pigs, cattle, horses, sheep, and goats, and pet animals such as dogs and cats, preferably humans.

The DNA aptamer for IFN-γ of the present invention consists of the nucleotide sequence as shown in any of SEQ ID NOs: 6 and 8 to 11. Particularly, the DNA aptamer for IFN-γ of the present invention consists of the nucleotide sequence as shown in SEQ ID NO: 8 or 9.

6. DNA Aptamer for VEGF

The fifth embodiment of the present invention relates to a DNA aptamer for vascular endothelial growth factor (abbreviated to "VEGF" in the present specification).

VEGF is a growth factor that functions as an angiogenic factor and is known as a causative factor of age-related macular degeneration (AMD).

The age-related macular degeneration is a progressive retinal disease that brings about severe symptoms such as decreased visual performance or acquired blindness in adult humans. This disease has been found to be aggravated and to be severe with progress in angiogenesis in the retina (Martin A. et al., 2003, Medicinal Research Reviews, Vol. 23, No. 2: 117-145; and Ferris III, F. L. et al., 1984, Archives of Ophthalmology, Vol. 102, Issue 11: 1640-1642).

The DNA aptamer for VEGF of the present invention is a DNA aptamer comprising a single-stranded DNA molecule that strongly and specifically binds to VEGF as a target substance and inhibits the angiogenic function of VEGF (hereinafter, this DNA aptamer is referred to as a "DNA aptamer for VEGF"). The organism species from which the target molecule VEGF of the DNA aptamer for VEGF of the present invention is derived is not limited. Examples thereof include VEGF from mammals, for example, primates such as humans and chimpanzee, laboratory animals such as rats and mice, livestock animals such as pigs, cattle, horses, sheep, and goats, and pet animals such as dogs and cats, preferably humans.

The DNA aptamer for VEGF of the present invention consists of the nucleotide sequence as shown in any of SEQ ID NOs: 19 to 22. Particularly, the DNA aptamer for VEGF of the present invention consists of the nucleotide sequence as shown in SEQ ID NO: 20 or 22.

7. DNA Aptamer for vWF

The sixth embodiment of the present invention relates to a DNA aptamer for von Willebrand factor (abbreviated to "vWF" in the present specification), particularly, a DNA aptamer for vWF A1 domain.

The DNA aptamer for vWF of the present invention is a DNA aptamer comprising a single-stranded DNA molecule that strongly and specifically binds to vWF, particularly, vWF A1 domain, as a target substance (hereinafter, this DNA aptamer is referred to as a "DNA aptamer for vWF"). The organism species from which the target molecule vWF of the DNA aptamer for vWF of the present invention is derived is not limited. Examples thereof include vWF from mammals, for example, primates such as humans and chimpanzee, laboratory animals such as rats and mice, livestock animals such as pigs, cattle, horses, sheep, and goats, and pet animals such as dogs and cats, preferably humans.

The DNA aptamer for vWF, particularly, vWF A1 domain, of the present invention consists of the nucleotide sequence as shown in any of SEQ ID NOs: 14 to 16. Particularly, the DNA aptamer for vWF, particularly, vWF A1 domain, of the present invention consists of the nucleotide sequence as shown in SEQ ID NO: 16.

8. Pharmaceutical Composition

The seventh embodiment of the present invention relates to a pharmaceutical composition.

8-1. Constitution

The pharmaceutical composition of the present invention comprises at least one DNA aptamer described in any of the third to sixth embodiments. The pharmaceutical composition of the present invention may also contain a pharmaceutically acceptable carrier. The "pharmaceutically acceptable carrier" refers to a substance that is usually used in the pharmaceutical formulating art and added without inhibiting or suppressing the effects of the pharmaceutical composition in order to facilitate the formulation of the pharmaceutical composition or its application to organisms and maintain the effect of the inhibitor of target substance function. Examples of the carrier include excipients, binders, disintegrants, fillers, emulsifiers, flow control additives, lubricants, and surfactants.

Examples of the "excipients" include sugars such as monosaccharides, disaccharides, cyclodextrin, and polysaccharides (specifically including, but not limited to, glucose, sucrose, lactose, raffinose, mannitol, sorbitol, inositol, dextrin, maltodextrin, starch, and cellulose), metal salts (e.g., sodium phosphate or calcium phosphate, calcium sulfate, and magnesium sulfate), citric acid, tartaric acid, glycine, low-, middle-, or high-molecular-weight polyethylene glycol (PEG), Plutonic, and combinations thereof.

Examples of the "binders" include starch glues composed of corn, wheat, rice, or potato starch, gelatin, tragacanth, methylcellulose, hydroxypropylmethylcellulose, sodium carboxymethylcellulose, and/or polyvinylpyrrolidone.

Examples of the "disintegrants" include the starches described above, carboxymethyl starch, cross-linked polyvinylpyrrolidone, agar, alginic acid or sodium alginate, and salts thereof.

Examples of the "fillers" include the sugars described above and/or calcium phosphate (e.g., tricalcium phosphate or calcium hydrogen phosphate).

Examples of the "emulsifiers" include sorbitan fatty acid ester, glycerin fatty acid ester, sucrose fatty acid ester, and propylene glycol fatty acid ester.

Examples of the "flow control additives" and the "lubricants" include silicate, talc, stearate, and polyethylene glycol.

Such carriers may be used appropriately according to the need. The pharmaceutical composition of the present invention may also contain, in addition to the additives described above, optional additives such as corrigents, solubilizing agents (solubilizers), suspending agents, diluents, surfactants, stabilizers, absorption promoters (e.g., quaternary ammonium salts and sodium lauryl sulfate), expanders, wetting agents, humectants (e.g. glycerin and starch), adsorbents (e.g., starch, lactose, kaolin, bentonite, and colloidal silicic acid), disintegration inhibitors (e.g., saccharose, stearin, cacao butter, and hydrogenated oil), coating agents, coloring agents, preservatives, antioxidants, fragrances, flavors, sweeteners, and buffers.

The "surfactants" correspond to, for example, alkali metal salts, alkaline earth metal salts, and ammonium salts of lignosulfonic, acid, naphthalenesulfonic acid, phenolsulfonic acid, or dibutylnaphthalenesulfonic acid, alkylaryl sulfonate, alkyl sulfate, alkyl sulfonate, fatty alcohol sulfate, fatty acid and sulfated fatty alcohol glycol ether, condensates of sulfonated naphthalene or naphthalene derivatives and formaldehyde, condensates of naphthalene or naphthalenesulfonic acid, phenol, and formaldehyde, polyoxyethylene octylphenyl ether, ethoxylated isooctylphenol, octylphenol, nonylphenol, alkylphenyl polyglycol ether, tributylphenyl polyglycol ether, tristearylphenyl polyglycol ether, alkylaryl polyether alcohol, alcohol and fatty alcohol/ethylene oxide condensates, ethoxylated castor oil, polyoxyethylene alkyl ether, ethoxylated polyoxypropylene, lauryl alcohol polyglycol ether acetal, sorbitol ester, lignosulfite waste liquors, and methylcellulose.

The pharmaceutical composition of this embodiment may contain one or more of these carriers per pharmaceutical composition.

The pharmaceutical composition of the present invention may further contain an additional drug without canceling the pharmacological effect of the nucleic acid of the present invention. The pharmaceutical composition of the present invention may contain, for example, a specific amount of an antibiotic.

The dosage form of the pharmaceutical composition of the present invention is not particularly limited as long as the form does not deactivate the active ingredient and can exert the pharmacological effect in vivo after administration. The dosage form usually varies depending on an administration method and/or prescription conditions.

Examples of dosage forms suitable for oral administration can include solid preparations (including tablets, pills, sublingual preparations, capsules, drops, and troches), granules, dusts, powders, and liquid preparations. The solid preparations can be prepared, if necessary, in coated dosage forms known in the art, for example, as sugar-coated tablets, gelatin-coated tablets, enteric coated tablets, film-coated tablets, bilayer tablets, or multilayer tablet.

Parenteral administration is subdivided into systemic administration and local administration. The local administration is further subdivided into interstitial administration, transepidermal administration, transmucosal administration, and transrectal administration. The pharmaceutical composition may also be prepared in a dosage form suitable for each administration method. Examples of dosage forms suitable for systemic or interstitial administration include injections which are liquid preparations. Examples of dosage forms suitable for transepidermal administration or transmucosal administration can include liquid preparations (including liniments, eye drops, nasal drops, and inhalants), suspensions (including emulsions and creams), dusts (including nasal drops and inhalants), pastes, gels, ointments, and plasters. Examples of dosage forms suitable for transrectal administration can include suppositories.

In the case of drug administration to plants, examples of the dosage form of the pharmaceutical composition include liquids, solids (including semi-solids), and combinations thereof. In this case, the pharmaceutical composition may be prepared as solutions, oil dispersions, emulsions, suspensions, dusts, powders, pastes, gels, pellets, tablets, and granules.

The specific shapes or sizes of these dosage forms are not particularly limited and may be any shape or size that falls within ranges accepted for each dosage form known in the art.

8-2. Production Method

The pharmaceutical composition of the present invention may be produced by the application of a formation method known in the art, as a rule. See a method described in, for example, Remington's Pharmaceutical Sciences (Merck Publishing Co., Easton, Pa.).

For example, the injection may be produced by a method routinely used in the art which involves dissolving the DNA aptamer of any of the third to sixth embodiments in a pharmaceutically acceptable solvent and, if necessary, adding a pharmaceutically acceptable carrier to the resulting solution.

Examples of the "pharmaceutically acceptable solvent" include water, ethanol, propylene glycol, ethoxylated isostearyl alcohol, polyoxygenated isostearyl alcohol, and polyoxyethylene sorbitan fatty acid esters. Desirably, such a solvent is sterilized and, if necessary, preferably adjusted to be isotonic to blood.

8-3. Administration Method

The pharmaceutical composition of this embodiment may be administered to an organism in a pharmaceutically effective amount for the treatment or prevention of the disease of interest or the like. The recipient organism is a vertebrate, preferably a mammal, more preferably a human.

The pharmaceutical composition of the present invention may be administered systemically or locally. An appropriate route can be selected according to, for example, the type, site of onset, or degree of progression of the disease. For a disease whose onset is localized to a site, local administration is preferred in which the pharmaceutical composition of the present invention is directly administered to the site of onset and its neighborhood through injection or the like. This is because the DNA aptamer of the present invention can be delivered in sufficient amounts to the site (tissue or organ) to be treated with little influence on the other tissues. For a disease whose site to be treated cannot be identified or a disease whose onset is systemic, systemic administration through intravenous injection or the like is preferred, though the administration route is not limited thereto. This is because the DNA aptamer of the present invention can be distributed throughout the body via blood flow and thereby delivered even to a lesion that cannot be found by diagnosis.

The pharmaceutical composition of the present invention may be administered by any appropriate method without deactivating the active ingredient. For example, any of parenteral (e.g., injection, aerosol, application, eye drop, and nasal drop) and oral administrations may be performed. Injection is preferred.

In the case of administration through injection, an injection site is not particularly limited. The injection site may be any site at which the DNA aptamer serving as an active ingredient can bind to the target substance to suppress its functions. Examples thereof include intravenous, intraarterial, intrahepatic, intramuscular, intraarticular, intramedullary, intraspinal, intraventricular, transpulmonary, transdermal, hypodermic, intradermal, intraperitoneal, intranasal, enteral, and sublingual injections, intravascular injection such as intravenous injection or intraarterial injection is preferred. This is because, as mentioned above, the pharmaceutical composition of the present invention can be distributed throughout the body via blood flow and also because this injection is relatively low invasive.

9. Method for Detecting Target Substance

The eighth embodiment of the present invention relates to a method for detecting a target substance using the DNA aptamer described in any of the third to sixth embodiments.

9-1. Constitution

The DNA aptamer described in any of the third to sixth embodiments is capable of very strongly and specifically binding to its target substance. The target substance present in a sample can therefore be detected by use of this property of the DNA aptamer.

The detection method itself can be any detection method known in the art as long as the method is based on the binding between the DNA aptamer described in any of the third to sixth embodiments and the target substance. For example, a SPR method, a quartz crystal microbalance method, turbidimetry, colorimetry, or fluorometry may be used.

SPR (surface plasmon resonance) refers to a phenomenon in which as a thin metal film is irradiated with laser beam, reflected light intensity remarkably attenuates at a particular angle of incidence (resonance angle). The SPR method is an assay method based on this phenomenon and is capable of highly sensitively assaying a substance adsorbed on the surface of the thin metal film serving as a sensor portion. In the present invention, for example, the target substance in the sample may be detected by immobilizing the DNA aptamer of any of the third to sixth embodiments in advance onto the surface of a thin metal film, flowing the sample on the thin metal film surface, and detecting the difference in the substance adsorbed on the metal surface between before and after the sample flowing resulted from the binding between the DNA aptamer and the target substance. SPR methods such as a displacement method and an indirect competitive method are known, any of which may be used in the present invention.

The QCM (quartz crystal microbalance) method refers to a method using a phenomenon in which the resonance frequency of a quartz crystal decreases according to the mass of the substance adsorbed onto the surface of electrodes attached to the quartz crystal. A QCM sensor based on this method can quantitatively capture a trace amount of the adsorbed substance according to the amount of change in the resonance frequency of a quartz crystal. In the present invention, the target substance in the sample can be quantitatively detected based on the amount of change in the resonance frequency of a quartz crystal resulted from the binding between the DNA aptamer and the target substance, by immobilizing the DNA aptamer advance, as in the SPR method, onto the electrode surface, and contacting a sample with the electrode surface. This technique is well known in the art. See, for example, Christopher J., et al. (2005), Self-Assembled Monolayers of a Form of Nanotechnology, Chemical Review, 105: 1103-1169.

The turbidimetry refers to a method which involves irradiating a solution with light and optically measuring the attenuation of light scattered by a substance floating in the solution or light transmitted through the solution using a colorimeter or the like to determine the amount of the substance in the solution. In the present invention, the target substance in the sample can be quantitatively detected by measuring absorbance before and after addition of the DNA aptamer of any of the third to sixth embodiments into a sample.

Alternatively, the target substance may be detected by combined use with an antibody against the target substance. For example, a method based on sandwich ELISA may be used. This method involves first immobilizing the DNA aptamer of any of the third to sixth embodiments onto a solid-phase carrier and next adding a sample thereto to allow the DNA aptamer to bind to the target substance present in the sample. Subsequently, the sample is washed off. Then, the anti-target substance antibody is added thereto and allowed to bind to the target substance. After washing, the target substance in the sample may be detected by detecting the anti-target substance antibody using an appropriately labeled secondary antibody. An insoluble carrier in the form of, for example, beads, a microplate, a test tube, a stick, or a test piece made of a material such as polystyrene, polycarbonate, polyvinyltoluene, polypropylene, polyethylene, polyvinyl chloride, nylon, polymethacrylate, latex, gelatin, agarose, cellulose, Sepharose, glass, a metal, a ceramic, or a magnetic material can be used as the solid-phase carrier.

EXAMPLES

Example 1: Preparation of DNA Aptamer Containing Mini-Hairpin Sequence

Figure 6:
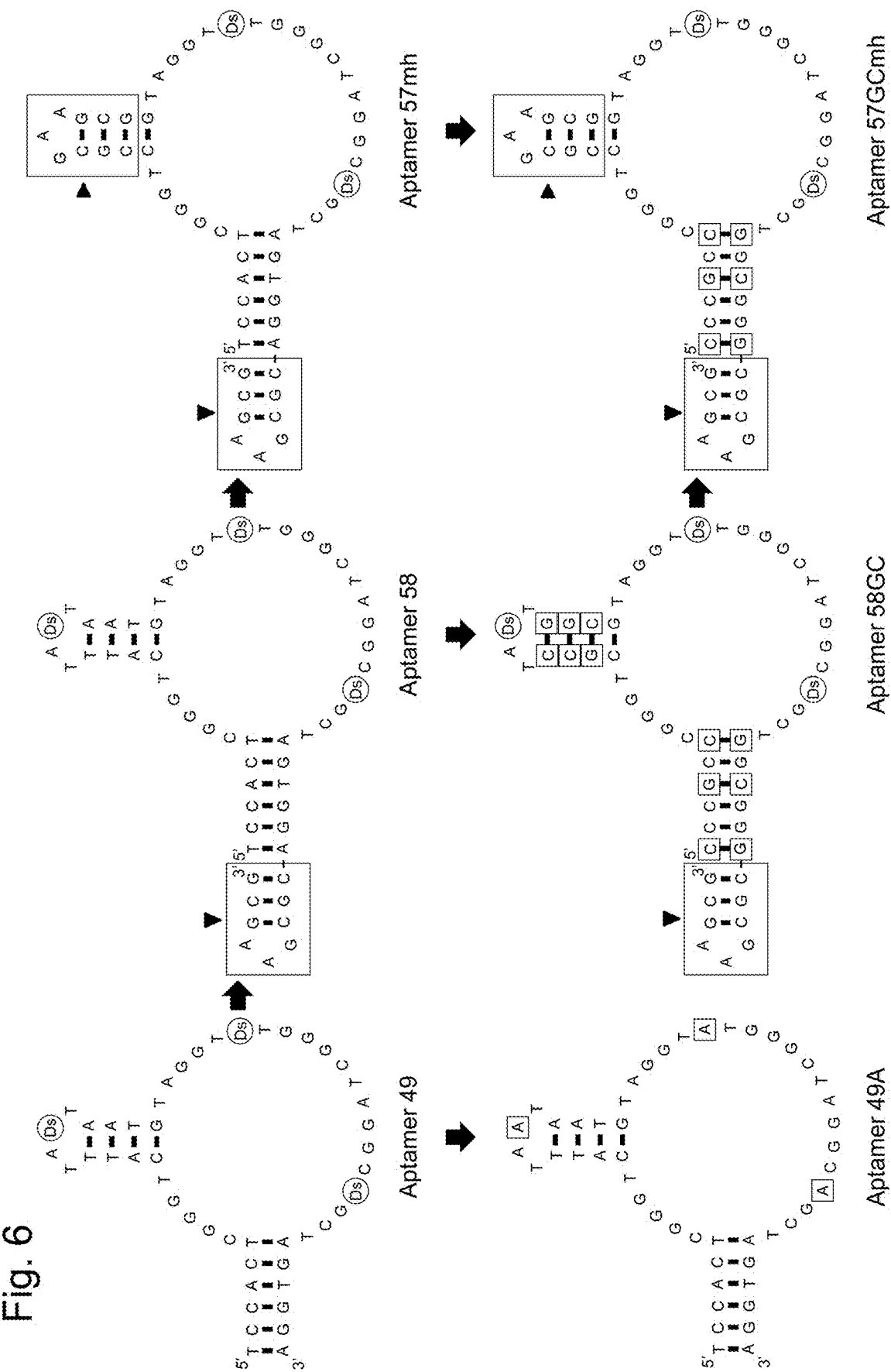
FIG. 6 is a diagram showing the sequence and secondary structure of each aptamer for IFN-γ prepared in Examples. The position of an artificial base Ds is circled. The site at which hairpin in the original Aptamer 49 was substituted with mini-hairpin and the site to which mini-hairpin was added are boxed with an arrowhead. The site at which an A-T base pair was substituted with a G-C base pair is boxed.

In order to examine whether the introduction of a mini-hairpin structure (short DNA fragment consisting of a sequence such as GCGNNACGC (SEQ ID NO: 23) or GCGNAGC (SEQ ID NO: 24) (N=A, T, G, or C)) and the substitution of A-T base pairs in a stem sequence with G-C base pairs are effective for the stability of a DNA aptamer, various nucleic acid fragments were first designed and prepared for DNA aptamers for human IFN-γ. The sequences of the aptamers prepared in this Example and their secondary structures are shown an FIG. 6.

Aptamer 49 (SEQ ID NO: 4) is a previously reported IFN-γ-binding DNA aptamer found by the inventors. Aptamer 49A (SEQ ID NO: 5) was derived from Aptamer 49 by the substitution of the artificial base Ds with the natural base A. Aptamer 58 (SEQ ID NO: 6) was derived from Aptamer 49 by the introduction of a mini-hairpin structure (short DNA fragment consisting of the sequence CGCGAAGCG (SEQ ID NO: 1)) to the 3' end. Aptamer 57mh (SEQ ID NO: 9) was derived from Aptamer 58 by the substitution of the internal hairpin of the sequence with a mini-hairpin structure (short DNA fragment consisting of the sequence CGCGAAGCG (SEQ ID NO: 1)). Aptamer 58GC (SEQ ID NO: 7) and Aptamer 57GCmh (SEQ ID NO: 8) were derived from Aptamer 58 and Aptamer 57mh by the substitution of A-T base pairs at two sites in the stem structure with G-C base pairs.

For Aptamer 49, Aptamer 58, Aptamer 58GC, Aptamer 57mh, Aptamer 57GCmh, and Aptamer 49A, each nucleic acid having the nucleotide sequence shown in the diagram was prepared by chemically synthesis and then purified on a denaturing acrylamide gel. Each nucleic acid fragment was heated at 95° C. for 3 minutes in a phosphate buffer solution (pH 7.4), then left standing at room temperature for 10 minutes for slow cooling, and left standing for 5 minutes on ice for reconstruction to prepare the DNA aptamer.

Example 2: Analysis on Binding Activity of Each Aptamer for IFN-γ Against Human IFN-γ

In order to examine each prepared nucleic acid prepared in Example 1 for its binding to human IFN-γ, a competition test was conducted using Aptamer 49 containing the artificial base Ds. In 20 μL of a reaction solution (1×PBS and 0.005% Nonidet P-40), Aptamer 49 labeled with [γ-$^{32}$P]ATP (final concentration: 200 nM), the aptamers prepared in Example 1 (final concentration 200 nM), and human IFN-γ (20 nM, PeproTech, Inc.) were mixed and incubated at 37° C. for 30 minutes. Then, 25% glycerol containing bromophenol blue was added thereto at a final glycerol concentration of 5%. Labeled Aptamer 49 bound to human IFN-γ was separated from labeled Aptamer 49 in a free form by 10% non-denaturing polyacrylamide gel electrophoresis. The gel was dried and visualized using Bio Image Analyzer FLA-7000 (Fujifilm), and the radioactivity was measured. The gel shift rate, the inhibition rate, and the relative binding rate were calculated as follows. The gel shift rate was calculated as the percentage of the value obtained by dividing the radioactivity of the complex by the total radioactivity of the free form and complex. The inhibition rate was calculated as the value obtained by subtracting, from 100, the percentage of the value obtained by dividing the gel shift rate in the presence of a competing aptamer by the gel shift rate in the absence of a competing aptamer. The relative binding rate was calculated by dividing the inhibition rate of each aptamer by the inhibition rate of Aptamer 49.

Three aptamers (Aptamer 49, Aptamer 58, and Aptamer 57GCmh) were further picked up from among the sequences prepared in Example 1 and their capacity to bind to human IFN-γ were analyzed by surface plasmon resonance (SPR) measurement using BIAcore T200 (GE Healthcare Japan Corp.).

First, a nucleic acid fragment having each sequence biotinylated at the end of the structure was chemically synthesized. In the same way as in Example 1, each nucleic acid fragment was then purified on a denaturing acrylamide gel, heated at 95° C. in a phosphate buffer solution (pH 7.4), and then slowly cooled to 25° C. for reconstruction to prepare the DNA aptamer. The SPR sensor chip used was a streptavidin-coated SA Chip (GE Healthcare Japan Corp.). Each DNA fragment was irreversibly immobilized onto the chip by a method given below and then analyzed for its binding to human IFN-γ. SPR was measured at a temperature set to 25° C. using a running buffer (1×PBS, +50 mM NaCl (final NaCl concentration: 205 mM), and 0.05% Nonidet P-40). For the immobilization of each DNA fragment onto the sensor chip, a DNA solution diluted with a PBS solution to 25 nM was subjected to folding treatment (denaturation by heating at 95° C. for 3 minutes followed by slow cooling to 25° C.), and diluted to 0.5 nM in tuning buffer, and Nonidet P-40 was then added thereto at a final concentration of 0.05%, and this DNA solution (40 μL) was injected to the SA chip at a flow rate of 5 μL/min (corresponding to 8 min). After the immobilization, DNA fragments nonspecifically adsorbed on the SA chip were washed off by the injection (5 μL×5) of a 50 mM NaOH solution at a flow rate of 20 μL/min. The interaction between the immobilized DNA fragment and human IFN-γ was detected under monitoring by the injection of 1.25 nM, 2.5 nM, 5 nM, 10 nM, 20 nM, 30 nM, and 50 nM human IFN-γ solutions (diluted with a running buffer) at the Kinetic Injection mode. The measurement conditions involved a flow rate of 100 μL/min and a protein injection time of 150 seconds. The regeneration of the chip (dissociation of bound proteins and DNA refolding) was performed by the injection of 5 μL (corresponding to 15 sec) of a 50 mM NaOH solution followed by the injection of a running buffer for 10 minutes. In order to cancel bulk effect on the sensor chip or response values attributed to nonspecific adsorption, the response value of a DNA-unimmobilized cell used as a reference cell was subtracted from the sensorgram of each DNA fragment.

<Results>

Figure 7:
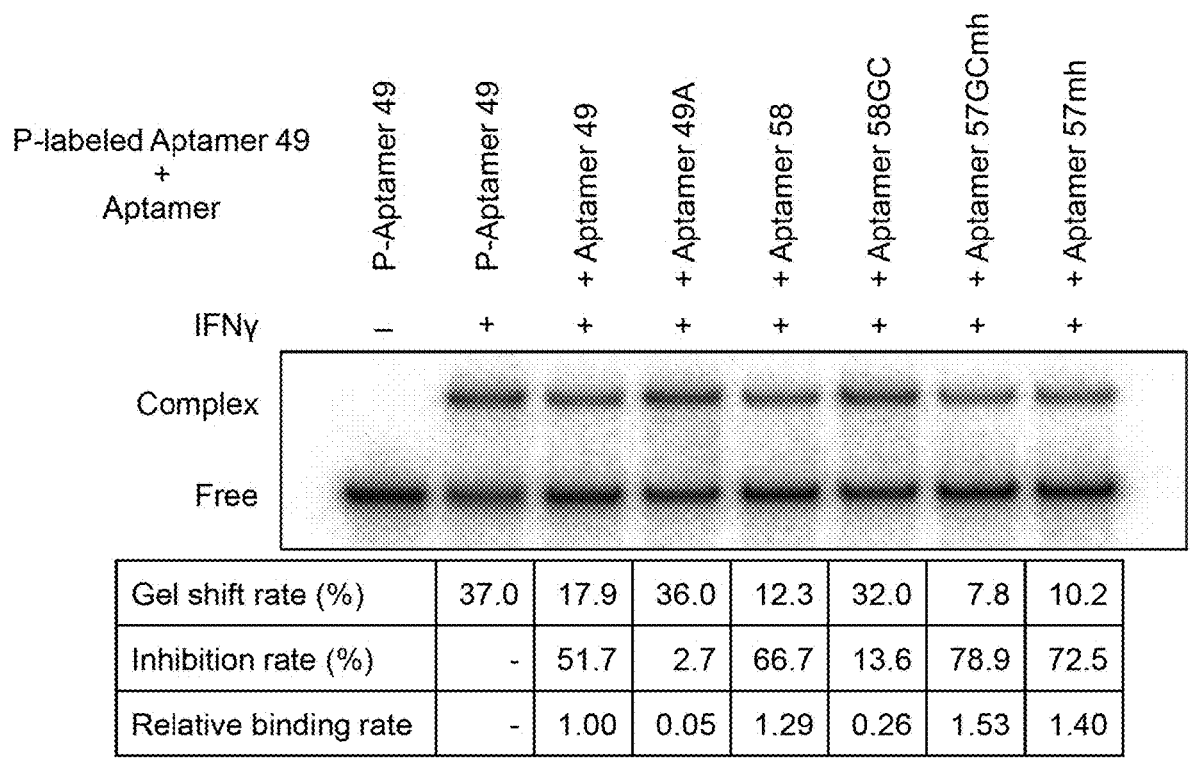
FIG. 7 is a diagram showing results of testing the competition of each aptamer for IFN-γ with Aptamer 49. The upper column shows each aptamer added together with P-labeled Aptamer 49 and the presence or absence of addition of IFN-γ (−: not added; +: added). The middle column shows the bands of a complex of P-labeled Aptamer 49 and IFN-γ and free P-labeled Aptamer 49. The lower column shows the gel shift rate, the inhibition rate of binding of Aptamer 49 to IFN-γ by each aptamer calculated from the gel shift rate, and the relative binding rate calculated by comparison with the competitive inhibitory capacity of Aptamer 49 itself.

The binding inhibition ratio of each aptamer variant to Aptamer 49 is shown in FIG. 7. When the binding inhibition ratio of the control Aptamer 49 was defined as 1.00, the relative binding rate of each aptamer variant containing the mini-hairpin structure was 0.05 (Aptamer 49A), 1.29 (Aptamer 58), 0.24 (Aptamer 58GC), 1.53 (Aptamer 57GCmh), and 1.40 (Aptamer 57mh). Aptamer 58, Aptamer 57mh, and Aptamer 57GCmh containing the mini-hairpin were shown to have significantly high binding strength, as compared with the control Aptamer 49. Among them, Aptamer 57GCmh in which a mini-hairpin was added to the 3' end, the internal hairpin portion was substituted with a mini-hairpin, and further, A-T base pairs in stem portions were substituted with G-C base pans had particularly high binding strength.

Figure 8:
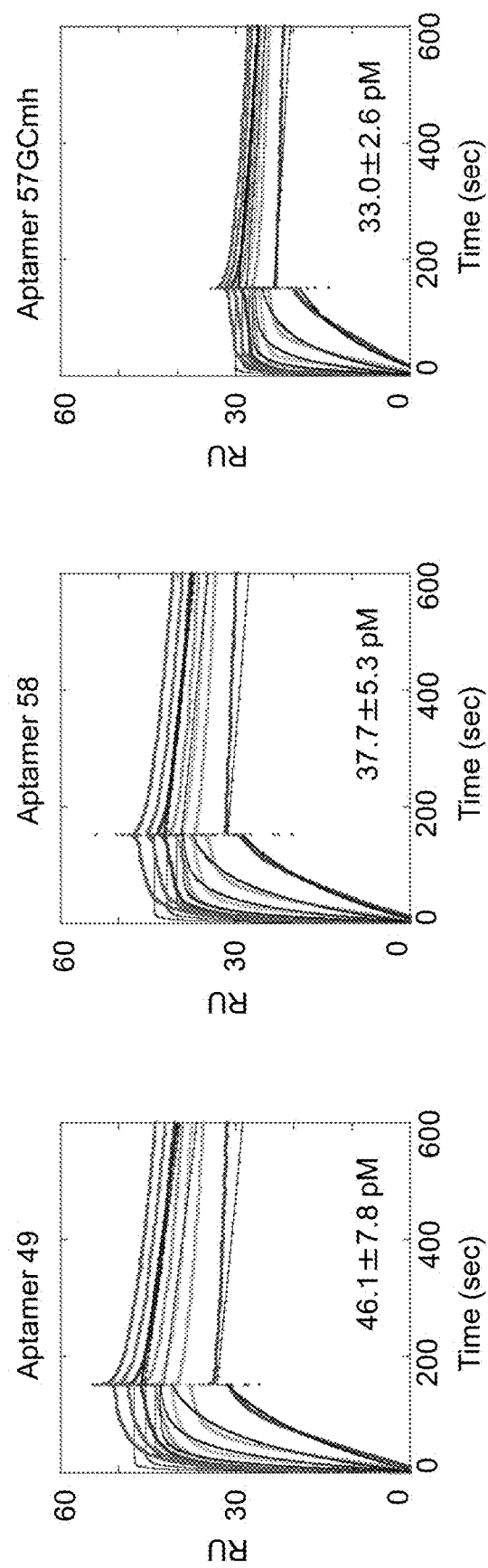
FIG. 8 is a diagram showing results of measuring the binding of each aptamer for IFN-γ to human IFN-γ by surface plasmon resonance. The abscissa shows time (sec). The ordinate shows resonance unit (RU). The numeric value in the diagram denotes a calculated Kd value.

The results of the SPR measurement are shown in FIG. 8. The KD value of each oligo was 46 pM (Aptamer 49), 38 pM (Aptamer 58), and 33 pM (Aptamer 57GCmh). These results demonstrated that binding strength can be improved by adding mini-hairpin DNA to the 3' end, further substituting internal hairpin with mini-hairpin DNA, and further substituting A-T base pairs in stem portions with G-C base pairs.

Example 3: Analysis on Stability of Each Aptamer for IFN-γ Against Nucleolytic Enzyme, Etc.

<Method>

Nucleolytic enzymes contained in serum are one of the main causes of DNA degradation, which hinders the biological application of nucleic acids. In this respect, each DNA aptamer containing the mini-hairpin structure was examined for its stability against nucleolytic enzymes contained in human serum.

Each DNA aptamer (Aptamer 49 Aptamer 58, Aptamer 57mh, and Aptamer 57GCmh; final concentration: 2 μM) was mixed with human serum at a concentration of 96%, and the mixture was incubated at 37° C. After 0 hours, 1 hour, 6 hours, 24 hours, 48 hours, and 72 hours, 10 μL was sampled from the mixed solution, and the degradation reaction was terminated by mixing with 110 μL of 1×TBE and a 10 M Urea solution. Each sample thus reacted was fractionated by 15% denaturing polyacrylamide gel electrophoresis. Then, the gel was stained with SYBR GOLD to detect a single-stranded nucleic acid. The band pattern of a product degraded by the nucleolytic enzymes in the human serum was analyzed using Bio Imager LAS-4000 (Fijifilm Corp). The amount of residual DNA was predicted from the density of a band corresponding to an undegraded aptamer.

<Results>

Figure 9:
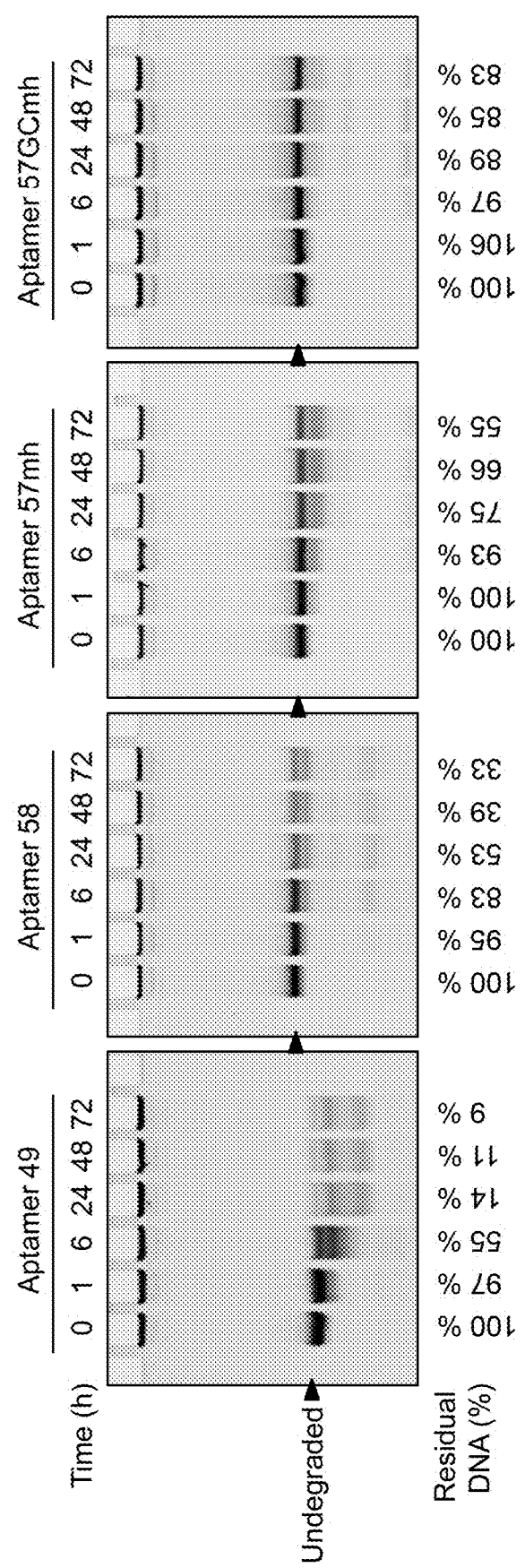
FIG. 9 is a diagram showing results of confirming the stability of each aptamer for IFN-γ in human serum by gel electrophoresis. The position of the band of an undegraded aptamer is indicated by a black triangle. Residual DNA at each time was calculated in percentage from the band of an undegraded aptamer electrophoresed after 0 hours, 1 hour, 6 hours, 24 hours, 48 hours, and 72 hours.

The results are shown in FIG. 9. The band corresponding to the full-length product of the control DNA aptamer (Aptamer 49) was degraded to 55% after 6 hours in the presence of human serum. The band corresponding to the full-length product was degraded to 14% after 24 hours and further degraded to 9% after 72 hours. On the other hand, the DNA aptamers containing the mini-hairpin DNA (Aptamer 58, Aptamer 57mh, and Aptamer 57GCmh) were confirmed, from their band patterns, to still retain 30% or more of the whole amount in the state of a full-length product even after 72 hours in the presence of human serum. Among them, 80% or more product of Aptamer 57GCmh in which a mini-hairpin was added to the 3' end, the internal hairpin portion was substituted with mini-hairpin DNA, and further, A-T base pairs in stem portions were substituted with G-C base pairs maintained the full length even after 72 hours in the presence of human serum, demonstrating that stability against nucleolytic enzymes, etc., contained in human serum is remarkably enhanced by, for example, the addition of mini-hairpin DNA.

Example 4: Analysis on Thermal Stability of Each Aptamer for IFN-γ

<Method>

The thermal stability of each DNA aptamer (Aptamer 49, Aptamer 49A, Aptamer 58, Aptamer 58GC, Aptamer 57mh, and Aptamer 57GCmh; final concentration: 2 μM) was studied by the measurement of a Tm value. Change in the absorbance of the DNA aptamer caused by the elevation of temperature (0.5° C./min) was measured using an ultraviolet and visible spectrophotometer UV-2450 (Shimadzu Corp.). The melting temperature (Tm value) was calculated from the first derivation thereof.

<Results>

Figure 10:
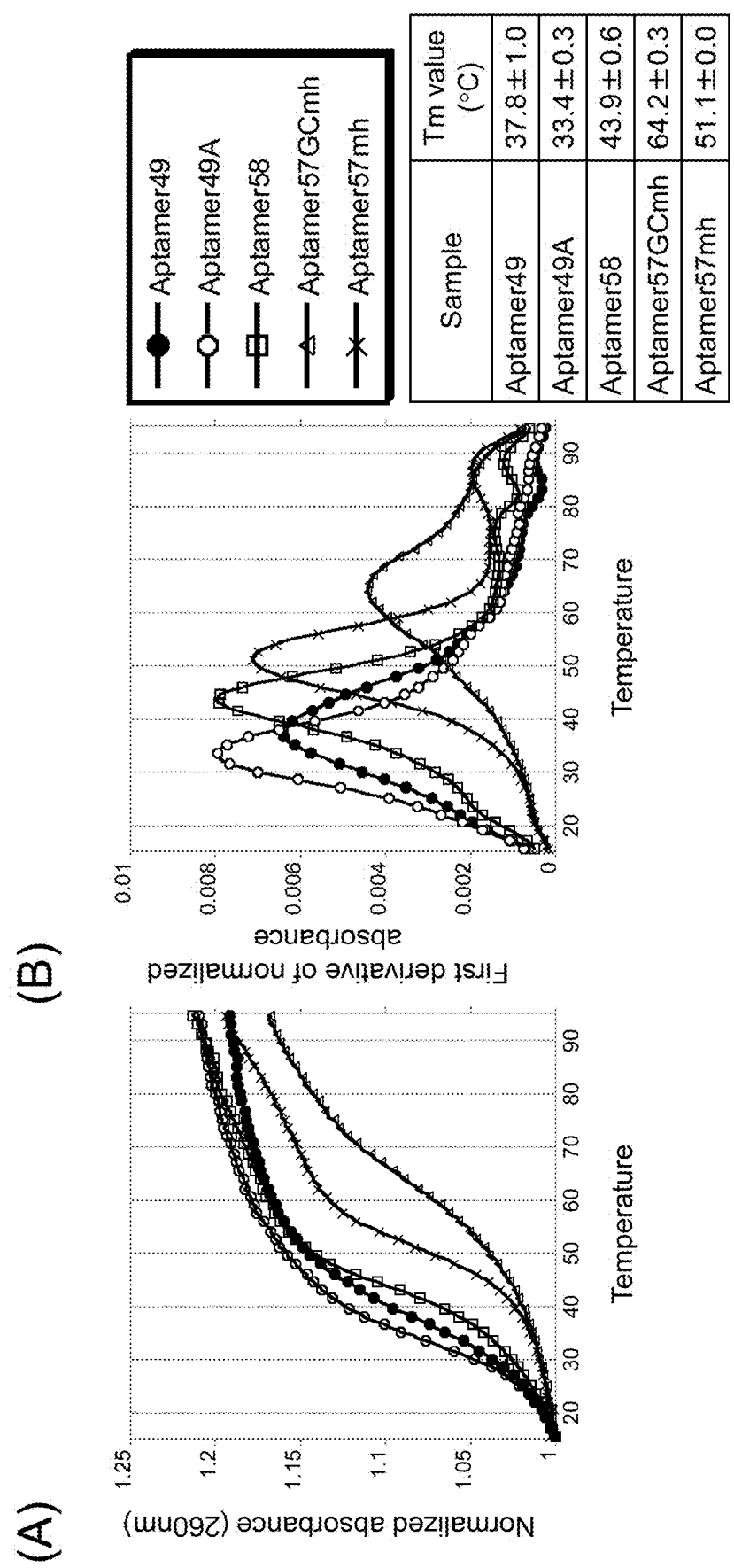
FIG. 10 is a diagram showing results of measuring the Tm value of each aptamer for IFN-γ.

The results are shown in FIG. 10. The control DNA aptamer (Aptamer 49) had a Tm value of 37.8° C., whereas the DNA aptamer containing no artificial base (Aptamer 49A) had a Tm value of 33.4° C. The Ds aptamer variants containing the mini-hairpin structure had a Tm value of 43.9° C. (Aptamer 58), 72.0° C. (Aptamer 58GC), 51° C. (Aptamer 57mh), and 64.2° C. (Aptamer 57GCmh). These results demonstrated that the addition of mini-hairpin DNA to the DNA aptamer remarkably increases the Tm value and improves the thermal stability. These results also demonstrated that the substitution of A-T base pairs in stem sequences with G-C base pairs further increases the Tm value.

Example 5: Analysis on Inhibitory Effect of Each Ds Aptamer on Cultured Cell in Response to IFN-γ Stimulation In this Example, the degree of phosphorylation of STAT-1 in response to IFN-γ stimulation was analyzed in the presence of each prepared DNA aptamer to examine the inhibitory effect of each aptamer on the interaction between IFN-γ and IFN-γ receptor.

<Method>

1) Cell Culture

MDA-MB-231 cells were cultured using a DMEM medium (Dulbecco's Minimal Essential Medium, Corning cellgro) containing 10% fetal bovine serum (FBS, Atlanta Biologicals, Inc.) and supplemented with a 100× solution of antibiotics (penicillin and streptomycin) and L-glutamine (Gibco/Life Technologies Corp.).

2) Stimulation Treatment with IFN-γ

For pretreatment of stimulation with IFN-γ, a DMEM medium containing 10% FBS and $10^6$ cells/mL of MDA-MB-231 cells was placed in a round polystyrene tube (Falcon/Becton, Dickinson and Company) and incubated at 37° C. for 15 minutes. Then, the cells were harvested by centrifugation at 1200 g for 5 minutes, then resuspended in a DMEM medium containing 2 ng/mL of a recombinant protein human IFN-γ (PeproTech, Inc.), and incubated at 37° C. for 10 minutes for stimulation with IFN-γ. Then, the cells were harvested by centrifugation, and then the stimulation was terminated by washing once with PBS to prepare cells after FACS analysis.

3) Stimulation Treatment with IFN-γ in Presence of Aptamer

In the same way as in the preceding paragraph 2), for pretreatment of stimulation, a DMEM medium containing 10% FBS and $10^6$ cells/mL of MDA-MB-231 cells was placed in a round polystyrene tube (Falcon/Becton, Dickinson and Company) and incubated at 37° C. for 15 minutes. Then, the cells were harvested by centrifugation at 1200 g for 5 minutes, then resuspended in a medium containing serum and each aptamer, and incubated overnight at room temperature or 37° C. On the following morning, IFNγ was added thereto, and the cells were incubated at 37° C. for 10 minutes for stimulation. Then, the cells were harvested by centrifugation, and then the stimulation was terminated by washing once with PBS to prepare cells for FACS analysis.

4) Preparation of Cell for FACS Analysis

The cells thus stimulated with IFN-γ and washed with PBS were suspended in 1 mL of a 2% paraformaldehyde solution (Electron Microscopy Sciences) and incubated at room temperature for 10 minutes. Then, the cells were harvested by centrifugation. The harvested cells were resuspended in 1 ml of 90% cooled methanol and incubated for 30 minutes to 60 minutes or overnight at 4° C. under dark conditions. The cells harvested by centrifugation were washed twice with 0.5 mL of a buffer solution for FACS analysis (containing 1×PBS, pH 7.4, 0.1% sodium azide, and 0.1% BSA), then incubated for 30 minutes to 60 minutes at 4° C. under dark conditions in 0.1 mL of a buffer solution for FACS analysis containing 7.5 µL of an anti-phosphorylated STAT-1 antibody solution (BD Phosflow PE mouse anti-Stat-1 pY701), and washed twice with 0.5 mL of a buffer solution for FACS analysis. The cells thus washed were suspended in 0.5 mL of a buffer solution for FACS analysis and then analyzed by flow cytometry.

<Results>

As a result of reacting the MDA-MB-231 cells with IFN-γ at a concentration of 2 ng/mL at 37° C. for 10 minutes and conducting FACS analysis using an anti-phosphorylated STAT-1 antibody, evident increase in fluorescence intensity induced by the anti-phosphorylated STAT-1 antibody in response to IFN-γ stimulation was confirmed (FIG. 11).

Figure 12:
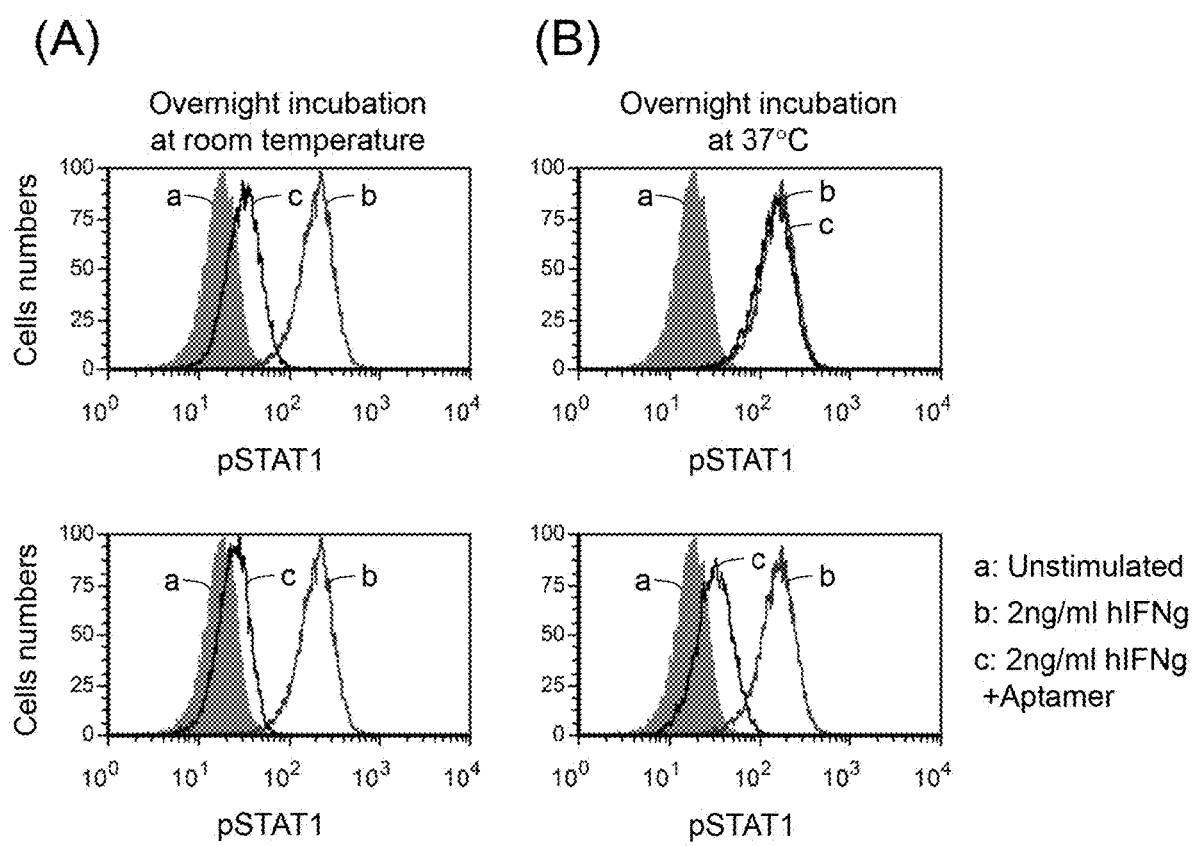
FIG. 12 is a diagram showing results of measuring the inhibitory effect of each aptamer for IFN-γ on response to IFN-γ stimulation by FACS using cultured cells. The abscissa shows fluorescence intensity. The ordinate shows the number of cells. The upper panels show the inhibitory effect of Aptamer 49. The lower panels show the inhibitory effect of Aptamer 58.

Next, Aptamer 49 and Aptamer 58 in which mini-hairpin DNA was added to the 3' end were used and each added at a nucleic acid concentration of 100 ng/mL to MDA-MB-231 cells at room temperature or at a reaction temperature of 37° C. After overnight incubation, the cells were reacted with IFN-γ for 10 minutes and analyzed by FACS using an anti-phosphorylated STAT-1 antibody. At room temperature, Aptamer 49 and Aptamer 58 were both confirmed to inhibit the phosphorylation of STAT1 (FIG. 12A). This demonstrated that the IFN-γ stimulation inhibitory activity of an aptamer is maintained even if mini-hairpin DNA is added to the 3' end. At 37° C., Aptamer 49 was degraded by nucleolytic enzymes, etc., contained in the medium and thereby lost its IFN-γ stimulation inhibitory effect, whereas Aptamer 58 was shown to maintain its IFN-γ stimulation inhibitory effect (FIG. 12B). From this, the addition of mini-hairpin DNA was confirmed to remarkably improve the stability against nucleolytic enzymes contained in serum in a medium.

Figure 13:
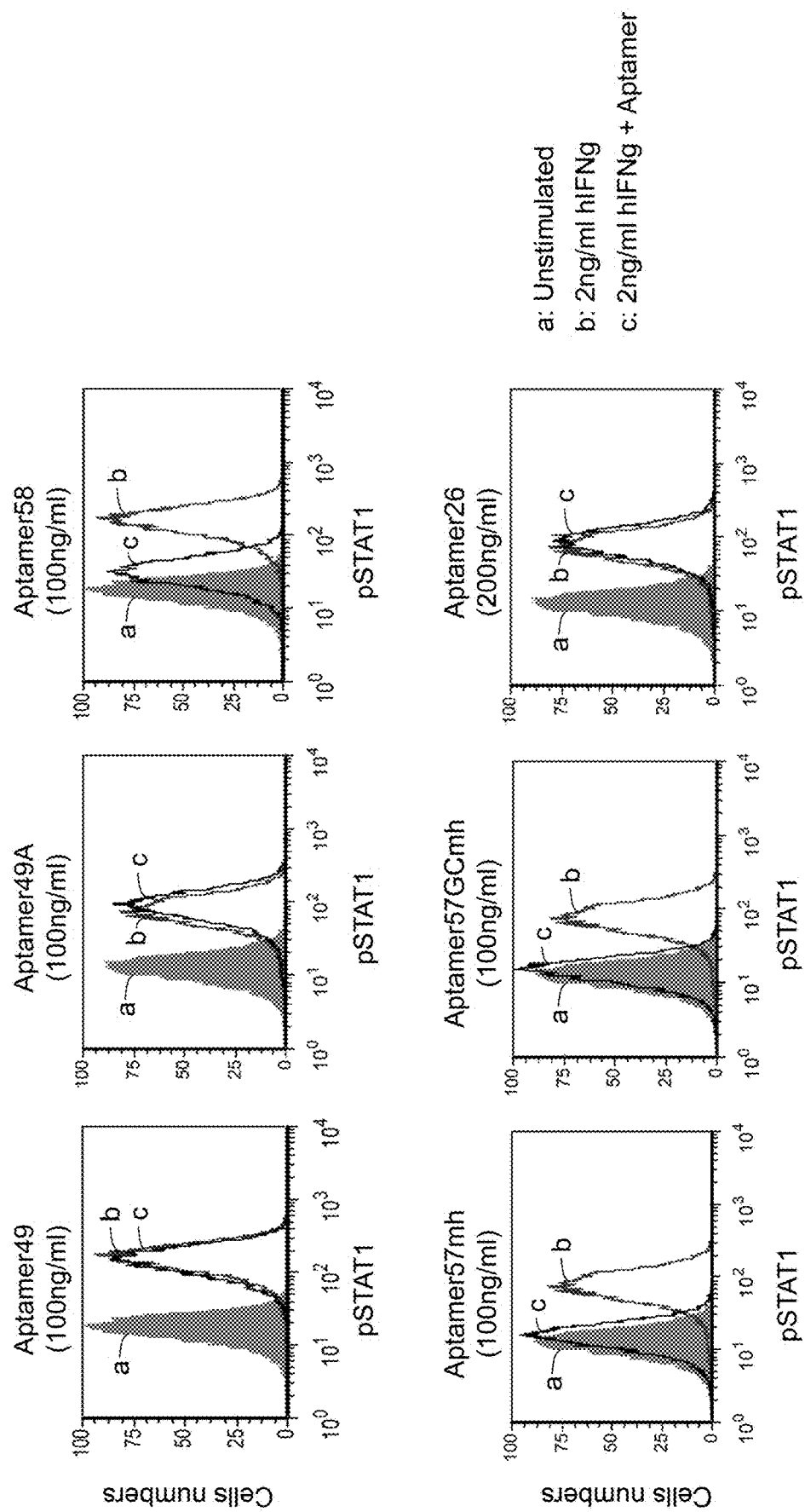
FIG. 13 is a diagram showing results of measuring the inhibitory effect of each aptamer for IFN-γ on response to IFN-γ stimulation by FACS using cultured cells. The abscissa shows fluorescence intensity. The ordinate shows the number of cells.

Next, each DNA aptamer (Aptamer 49, Aptamer 49A, Aptamer 58, Aptamer 57mh, and Aptamer 57GCmh) and an existing DNA aptamer for IFN-γ as a control (Aptamer 26) were used and examined for their IFN-γ stimulation inhibitory effects. Each aptamer was added at a concentration of 100 to 200 ng/mL and reacted overnight at 37° C., followed by FACS analysis using an anti-phosphorylated STAT-1 antibody. The control Aptamer 26, and Aptamer 49 and Aptamer 49A to which no mini-hairpin DNA was added hardly exhibited an IFN-γ stimulation inhibitory effect, whereas Aptamer 58, Aptamer 57mh, and Aptamer 57GCmh to which mini-hairpin DNA was added were confirmed to exhibit an IFN-γ stimulation inhibitory effect. Particularly, Aptamer 57mh and Aptamer 57GCmh in which mini-hairpin DNA was added to the 3' end and the internal hairpin portion was substituted with mini-hairpin DNA remarkably maintained their IFN-γ stimulation inhibitory effects and were thus found to have the evidently improved stability by the addition of mini-hairpin DNA (FIG. 13).

Example 6: Analysis on Binding Activity of Aptamer for IFN-γ Consisting of Natural Bases Against Human IFN-γ

In this Example, a DNA aptamer consisting of natural bases without containing artificial bases was examined for whether the addition of mini-hairpin DNA and the addition of GC pairs to the stem structure could also improve its binding activity.

<Method>

Figure 14:
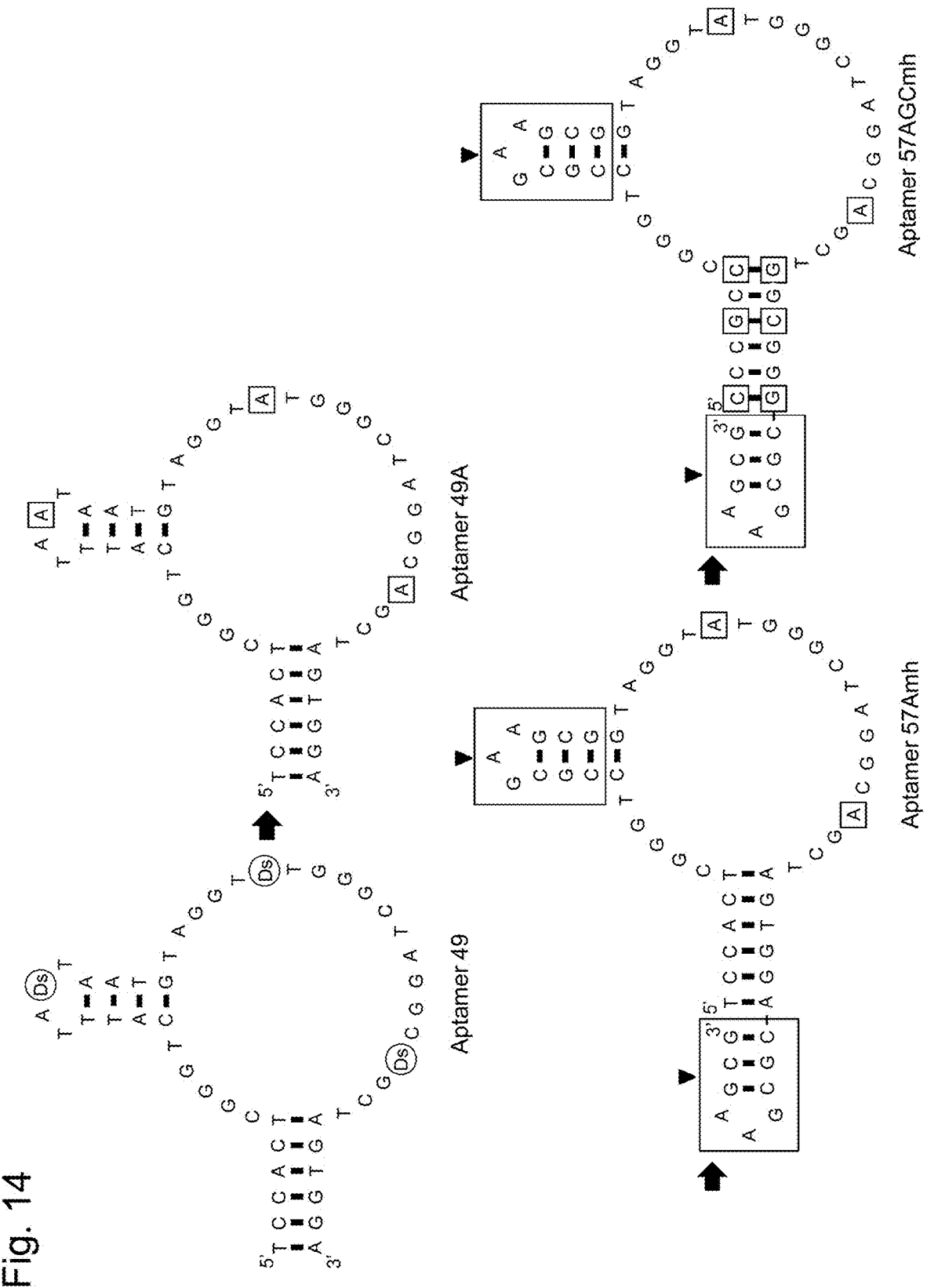
FIG. 14 is a diagram showing the sequence and secondary structure of each aptamer for IFN-γ consisting of natural bases, prepared in Examples. The position of an artificial base Ds is circled. The site at which hairpin in the original Aptamer 49 was substituted with mini-hairpin and the site to which mini-hairpin was added are boxed with an arrowhead. The site at which an artificial base Ds was substituted with A and the site at which an A-T base pair was substituted with a G-C base pair are indicated by small boxes.

A nucleic acid having each nucleotide sequence shown in FIG. 14 was prepared by chemical synthesis.

As described above, Aptamer 49 (SEQ ID NO: 4) is a previously reported IFN-γ-binding DNA aptamer found by the inventors. Aptamer 49A (SEQ ID NO: 5) was derived from Aptamer 49 by the substitution of the artificial base Ds with the natural base A. Aptamer 57Amh (SEQ ID NO: 11) was derived from Aptamer 49A by the introduction of a mini-hairpin structure to the 3' end and the substitution of the internal hairpin of the sequence with a mini-hairpin structure (short DNA fragment consisting of the sequence CGC-GAAGCG (SEQ ID NO: 1)). Aptamer 57AGCmh (SEQ ID NO: 10) was derived from Aptamer 57Amh by the substitution of A-T base pairs at two sites in the stem structure with G-C base pairs.

In the same way as in Example 1, each nucleic acid consisting of the nucleotide sequence described above was chemically synthesized, purified, and reconstructed to prepare each DNA aptamers.

In order to examine each prepared nucleic acid for its binding to human IFN-γ, a competition test was conducted using Aptamer 49, which was a wild-type aptamer containing the artificial base Ds. In 20 μL of a reaction solution (1×PBS and 0.005% Nonidet P-40), Aptamer 49 labeled with [γ-$^{32}$P]ATP (final concentration: 20 nM), a 1000-fold amount of each unlabeled nucleic acid (Aptamer 49A, Aptamer 57AGCmh, and Aptamer 57Amh) (final concentration: 20 μM), and human IFN-γ (20 nM, PeproTech, Inc.) were mixed and incubated at 37° C. for 30 minutes. Then, 25% glycerol containing bromophenol blue was added thereto at a final glycerol concentration of 5%. Labeled Aptamer 49 bound to human IFN-γ was separated from labeled Aptamer 49 in a free form by 10% non-denaturing polyacrylamide gel electrophoresis. The gel was dried and visualized using Bio Image Analyzer FLA-7000, and the radioactivity was measured. The gel shift rate, the inhibition rate, and the relative binding rate were calculated in accordance with Example 2.

<Results>

Figure 15:
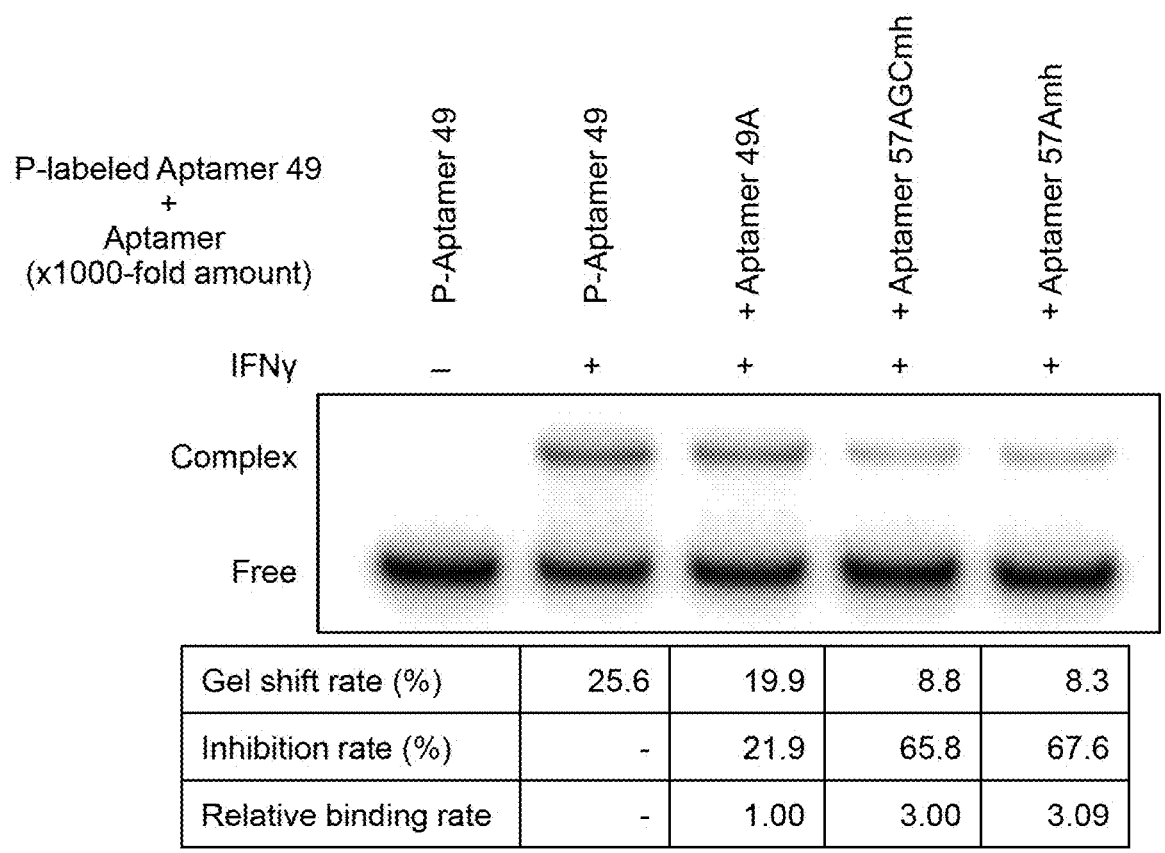
FIG. 15 is a diagram showing results of testing competition with Aptamer 49. The upper column shows each aptamer added together with P-labeled Aptamer 49 and the presence or absence of addition of IFN-γ (−: not added; +: added). The middle column shows the bands of a complex of P-labeled Aptamer 49 and IFN-γ and free P-labeled Aptamer 49. The lower column shows the gel shift rate, the inhibition rate of binding of Aptamer 49 to IFN-γ by each aptamer calculated from the gel shift rate, and the relative binding rate calculated by comparison with the competitive inhibitory capacity of Aptamer 49 itself.

The binding inhibition ratio of each aptamer variant to Aptamer 49 is shown in FIG. 15. When the binding inhibition ratio of the control Aptamer 49A was defined as 1.00, the binding inhibition ratio (relative binding rate) of each aptamer variant containing the mini-hairpin structure was 3.00 (Aptamer 57AGCmh) and 3.09 (Aptamer 57Amh). Aptamer 57AGCmh and Aptamer 57Amh containing the mini-hairpin were shown to have significantly improved binding strength, as compared with the control Aptamer 49A.

Example 7: Analysis on Thermal Stability of Aptamer Consisting of Natural Bases for IFN-γ

<Method>

The thermal stability of each DNA aptamer consisting of natural bases (Aptamer 49A, Aptamer 57Amh, and Aptamer 57AGCmh; final concentration: 2 μM) was studied by the measurement of a Tm value. Change in the absorbance of the DNA aptamer caused by the elevation of temperature (0.5° C./min) was measured using an ultraviolet and visible spectrophotometer UV-2450 (Shimadzu Corp). The melting temperature (Tm value) was calculated from the first derivation thereof.

<Results>

The results are shown in FIG. 16. The control DNA aptamer (Aptamer 49A) had a Tm value of 33.4° C., whereas the aptamer variants consisting of natural bases containing the mini-hairpin structure had a Tm value of 45.4° C. (Aptamer 57Amh) and 61.6° C. (Aptamer 57AGCmh). These results demonstrated that the addition of mini-hairpin DNA to the DNA aptamer remarkably increases the Tm value and improves the thermal stability. These results demonstrated that the addition of mini-hairpin and the addition of GC improve the thermal stability of a DNA aptamer regardless of the presence or absence of the artificial base Ds.

Example 8: Analysis on Binding Activity of Aptamer for vWF Against vWF A1 Domain A DNA aptamer for a protein other than IFN-γ was examined for whether the addition of mini-hairpin DNA could improve its binding activity.
<Method>

Figure 17:
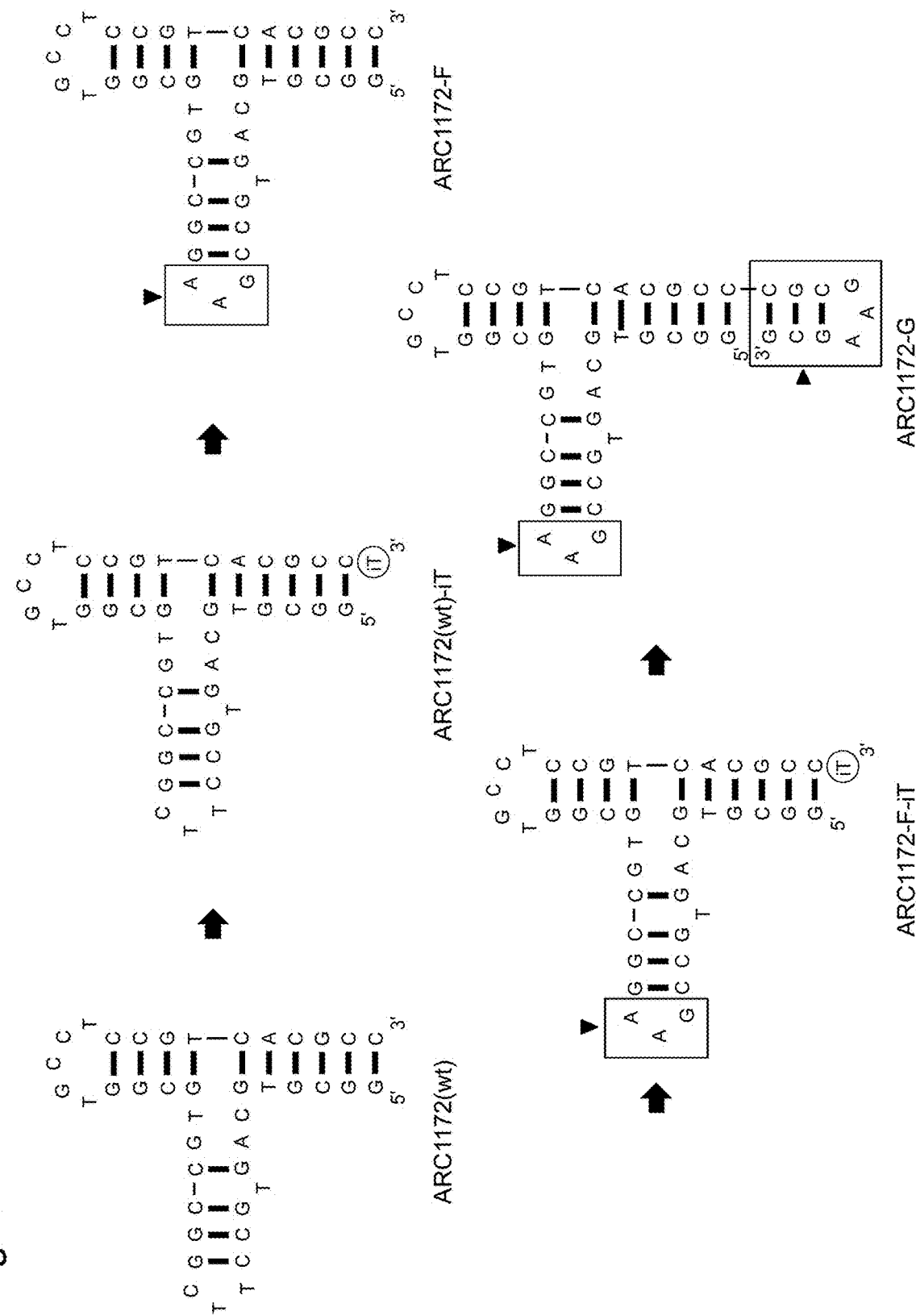
FIG. 17 is a diagram showing the sequence and secondary structure of each aptamer for vWF A1 domain prepared in Examples. The site at which hairpin in the original ARC1172 (wt) was substituted with mini-hairpin and the site to which mini-hairpin was added are boxed with an arrowhead. The position of inverted dT added to the end is circled.

A nucleic acid having each nucleotide sequence shown in FIG. 17 was prepared by chemical synthesis.

ARC1172(wt) (SEQ ID NO: 12) is a known vWF A1 domain-binding DNA aptamer. ARC1172(wt)-iT (SEQ ID NO. 13) was derived from ARC1172(wt) by the addition of inverted dT to the 3' end, which is a conventional technique of stabilizing nucleic acids. ARC1172-F (SEQ ID NO: 14) was derived therefrom by the substitution of the internal hairpin of the sequence with a mini-hairpin structure (short DNA fragment consisting of the sequence GCCGAAGGC (SEQ ID NO. 2)). ARC1172-F-iT (SEQ ID NO: 15) was derived from ARC1172-F by time addition of inverted dT to the 3' end, which is a conventional technique of stabilizing nucleic acids. ARC1172-G (SEQ ID NO: 16) was derived from ARC1172-F by the introduction of a mini-hairpin structure (short DNA fragment consisting of the sequence CGCGAAGCG (SEQ ID NO: 1)) to the 3' end.

In the same way as in Example 1, each nucleic acid consisting of the nucleotide sequence described above was chemically synthesized, purified, and reconstructed to prepare each DNA aptamers.

In order to examine each prepared nucleic acid for its binding to vWF A1 domain, competition with ARC1172 reported as an aptamer binding to vWF A1 domain was tested using each variant nucleic acid. In 20 μL of a reaction solution (1×PBS and 0.1 mg/mL BSA), ARC1172 labeled with [γ-$^{32}$P]ATP (final concentration: 100 nM), each unlabeled nucleic acid (ARC1172(wt), ARC1172(wt)-iT, ARC1172-F, ARC1172-F-iT, and ARC1172-G) (final concentration: 100 nM), and vWF A1 domain (100 nM, U-Protein Express BV) were mixed and incubated at 37° C. for 30 minutes. Then, 25% glycerol containing bromophenol blue was added thereto at a final glycerol concentration of 5%. Labeled ARC1172(wt) bound to vWF A1 domain was separated from labeled ARC1172 in a free form by 10% non-denaturing polyacrylamide gel electrophoresis. The gel was dried and visualized using Bio Image Analyzer FLA-7000, and the radioactivity was measured. The gel shift rate, the inhibition rate, and the relative binding rate were calculated in accordance with Example 2.

<Results>

Figure 18:
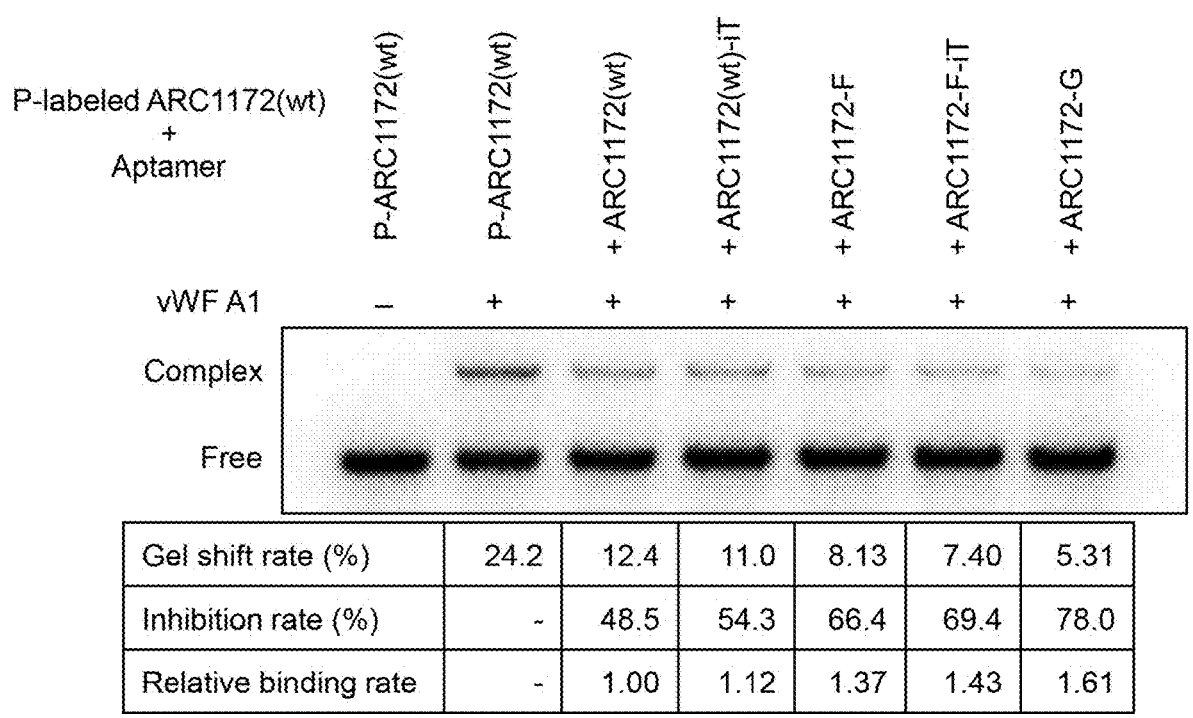
FIG. 18 is a diagram showing results of testing the competition of each aptamer for vWF A1 domain with ARC1172(wt). The upper column shows each aptamer added together with P-labeled ARC1172(wt) and the presence or absence of addition of vWF A1 (−: not added; +: added). The middle column shows the bands of a complex of P-labeled ARC1172(wt) and vWF A1 and free P-labeled ARC1172(wt). The lower column shows the gel shift rate, the inhibition rate of binding of ARC1172(wt) to vWF A1 domain by each aptamer calculated from the gel shift rate, and the relative binding rate calculated by comparison with the competitive inhibitory capacity of ARC1172(wt) itself.

The binding inhibition ratio of each aptamer variant labeled ARC1172(wt) is shown in FIG. 18. When the binding inhibition ratio of the control unlabeled ARC1172 (wt) was defined as 1.00, the binding inhibition ratios (relative binding rates) of the aptamer variants in which inverted dT was added to the 3' end and to which mini-hairpin DNA was added were 1.12 (ARC1172(wt)-iT), 1.37 (ARC1172-F), 1.43 (ARC1172-F-iT), and 1.61 (ARC1172-G). ARC1172-G in which the hairpin structure was substituted with a mini-hairpin structure and further mini-hairpin DNA was added to the 3' end was shown to have the most improved binding activity, as compared with the control ARC1172. These results demonstrated that binding strength can be improved by adding DNA to a conventional DNA aptamer consisting of natural bases.

Example 9: Analysis on Stability of Aptamer for vWF Against Nucleolytic Enzyme, Etc.

In this Example, a DNA aptamer consisting of natural bases to which mini-hairpin DNA was added was examined for its stability against nucleolytic enzymes contained in human serum. Also, this technique was comparatively studied with the addition of inverted dT to the 3' end, which is a conventional technique of stabilizing nucleic acids.
<Method>

Each DNA aptamer containing or not containing the mini-hairpin DNA (ARC11721(wt), ARC1172(wt)-iT, ARC1172-F, ARC1172-F-iT, and ARC1172-G, final concentration: 2 μM) was mixed with human serum at a concentration of 96%, and this solution was incubated at 37° C. After 0 hours, 1 hour, 6 hours, 24 hours, 48 hours, and 72 hours, 10 μL was sampled from the mixed solution, and the degradation reaction was terminated by mixing with 110 μL of 1×TBE and a 10 M Urea solution. Each sample thus reacted was fractionated by 15% denaturing polyacrylamide gel electrophoresis. Then, the gel was stained with SYBR GOLD to detect a single-stranded nucleic acid. The band pattern of a degradation product by the nucleolytic enzymes in the human serum was analyzed using Bio Imager LAS-4000 (Fujifilm Corp). The amount of residual DNA was predicted from the density of a band corresponding to an undegraded aptamer.

<Results>

Figure 19:
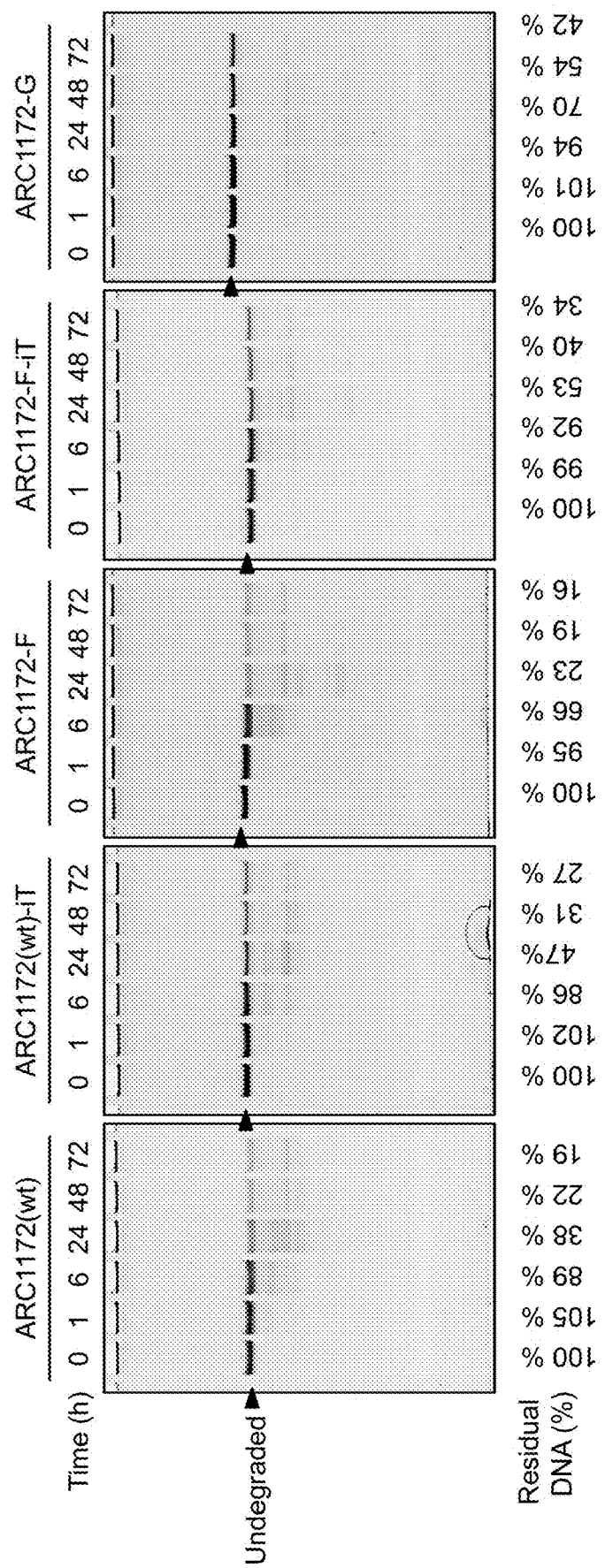
FIG. 19 is a diagram showing results of confirming the stability of each aptamer for vWF A1 domain in human serum by gel electrophoresis. The position of the band of an undegraded aptamer is indicated by a black triangle. Residual DNA at each time was calculated in percentage from the band of an undegraded aptamer electrophoresed after 0 hours, 1 hour, 6 hours, 24 hours, 48 hours, and 72 hours.

The results are shown in FIG. 19. The band corresponding to the full-length product of the control DNA aptamer (ARC1172(wt)) was degraded to 38% after 24 hours in the presence of human serum. The hand corresponding to the full-length product was degraded to 19% after 72 hours. As compared with ARC1172(wt), the DNA aptamer to which inverted dT was added in accordance with the conventional technique of stabilizing nucleic acids (ARC1172(wt)-iT) had improved stability against nucleolytic enzymes in human serum. Nonetheless, the band corresponding to its full-length product was degraded to 47% after 24 hours in the presence of human serum. The band corresponding to the full-length product was degraded to 27% after 72 hours. On the other hand, the DNA aptamer in which mini-hairpin DNA was added both to the 3' end and to the internal sequence (ARC1172-G) was confirmed, from its band pattern, to still retain 70% and 42% of the whole amount after 24 hours and after 72 hours, respectively, in the presence of human serum. This demonstrated that stability against nucleolytic enzymes, etc., contained in human serum is remarkably enhanced by the addition of mini-hairpin DNA. The addition of mini-hairpin DNA to the 3' end was shown to be more effective for improving stability against nucleolytic enzymes, etc., contained in human serum, than the addition of inverted dT to the 3' end (conventional technique of stabilizing nucleic acids).

Example 10: Analysis on Thermal Stability of Aptamer for vWF

<Method>

The thermal stability of each DNA aptamer (ARC1172 (wt), ARC1172(wt)-iT, ARC1172-F, ARC1172-F-iT, and ARC1172-G; final concentration: 2 μM) was studied by the measurement of a Tm value. Change the absorbance of the DNA aptamer caused by the elevation of temperature (0.5° C./min) was measured using an ultraviolet and visible spectrophotometer UV-2450 (Shimadzu Corp.). The melting temperature (Tm value) was calculated from the first derivation thereof.

<Results>

The results are shown in FIG. 20. The control DNA aptamer (ARC1172(wt)) had a Tm value of 63.8° C. whereas the DNA aptamer in which inverted dT was added to the 3' end in accordance with the conventional technique of stabilizing nucleic acids (ARC1172(wt)-iT) had a Tm value of 63.2° C. The Ds aptamer variants containing the structure had a Tm value of 64.3° C. (ARC1172-F), 64.4° C. (ARC1172-F-iT), and 61.9° C. (ARC1172-G). These results demonstrated that the addition of mini-hairpin DNA to the DNA aptamer neither largely changes the Tm value nor largely reduces the thermal stability.

Example 11: Design and Preparation of Aptamer for VEGF

Figure 21:
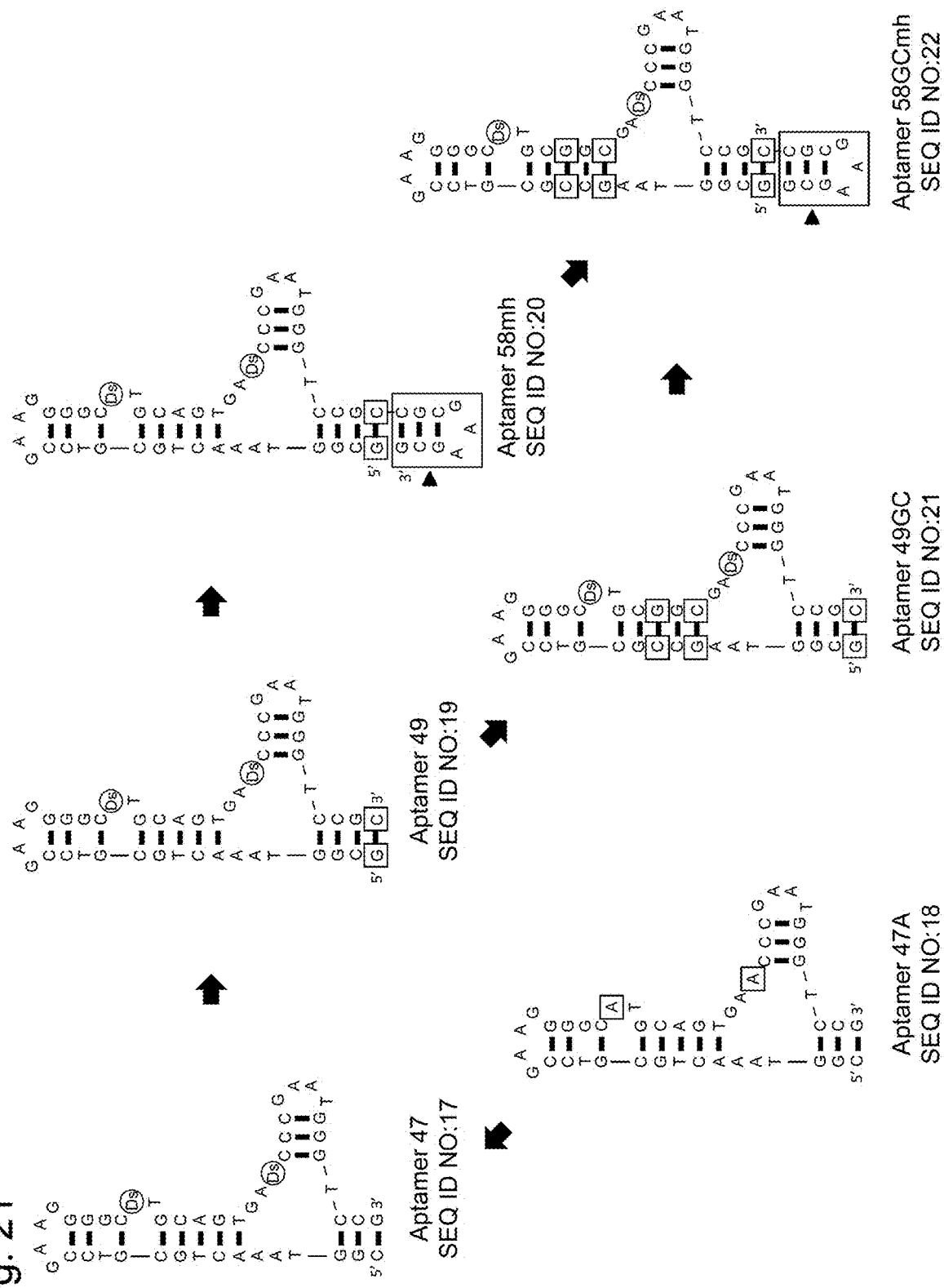
FIG. 21 shows the sequence and secondary structure of each aptamer for VEGF165 prepared in Examples. The position of an artificial base Ds is circled. The site at which a G-C base pair was added to the original Aptamer 47 and the site at which an A-T base pair was substituted with a G-C base pair are indicated by small boxes. A mini-hairpin sequence is boxed with an arrowhead.

In order to examine the influence of, for example, the addition of a mini-hairpin structure and GC pairs, on the characteristics of a VEGF-binding DNA aptamer, each anti-VEGF165 DNA aptamer variant shown in FIG. 21 was designed and prepared.

Aptamer 47 (SEQ ID NO: 17) is a previously reported VEGF-binding DNA aptamer found by the inventors. Aptamer 47A (SEQ ID NO: 18) was derived from Aptamer 47 by the substitution of the artificial base Ds with the natural base A. Aptamer 49 (SEQ ID NO: 19) was a variant derived from Aptamer 47 by the elongation of the terminal stem structure by one G-C base pair. Aptamer 58mh (SEQ ID NO: 20) was derived from Aptamer 49 by the further introduction of a mini-hairpin structure (short DNA fragment consisting of the sequence CGCGAAGCG (SEQ ID NO: 1)) to the 3' end. Aptamer 49GC (SEQ ID NO: 21) and Aptamer 58GCmh (SEQ ID NO: 22) were derived from Aptamer 49 and Aptamer 58 mh by the substitution of A-T base pairs at two sites in the stem structure with G-C base pairs, respectively.

Each variant was chemically synthesized. In the same way as in Example 1, each nucleic acid fragment was then purified by polyacrylamide electrophoresis, heated at 95° C. in a phosphate buffer solution (pH 7.4), and then slowly cooled to room temperature for reconstruction. The resulting DNA aptamer was then used in Examples below.

Example 12: Analysis on Binding Activity of Aptamer for VEGF Against Target Protein <Method>

In order to compare binding activity against human-derived VEGF165 protein among various aptamers prepared in Example 11, binding activity analysis was conducted by the competition experiment. This analysis was conducted at a scale of 20 μL. In a phosphate buffer solution (pH 7.4) containing 0.005% Nonidet P40, Aptamer 47 labeled with [γ-$^{32}$P]ATP (final concentration: 100 nM), each unlabeled variant (final concentration: 100 nM), and VEGF165 protein (PeproTech, Inc., final concentration: 100 nM) were mixed and incubated at 37° C. for 30 minutes. Then, 5 μl of 25% glycerol was added thereto. Immediately thereafter, labeled Aptamer 47 bound to VEGF165 protein was separated from free aptamer 47 by 10% non-denaturing polyacrylamide gel electrophoresis. The gel was dried and visualized using Bio Image Analyzer, and the radioactivity was measured. The gel shift rate, the inhibition rate, and the relative binding rate were calculated in accordance with Example 2.

<Results>

Figure 22:
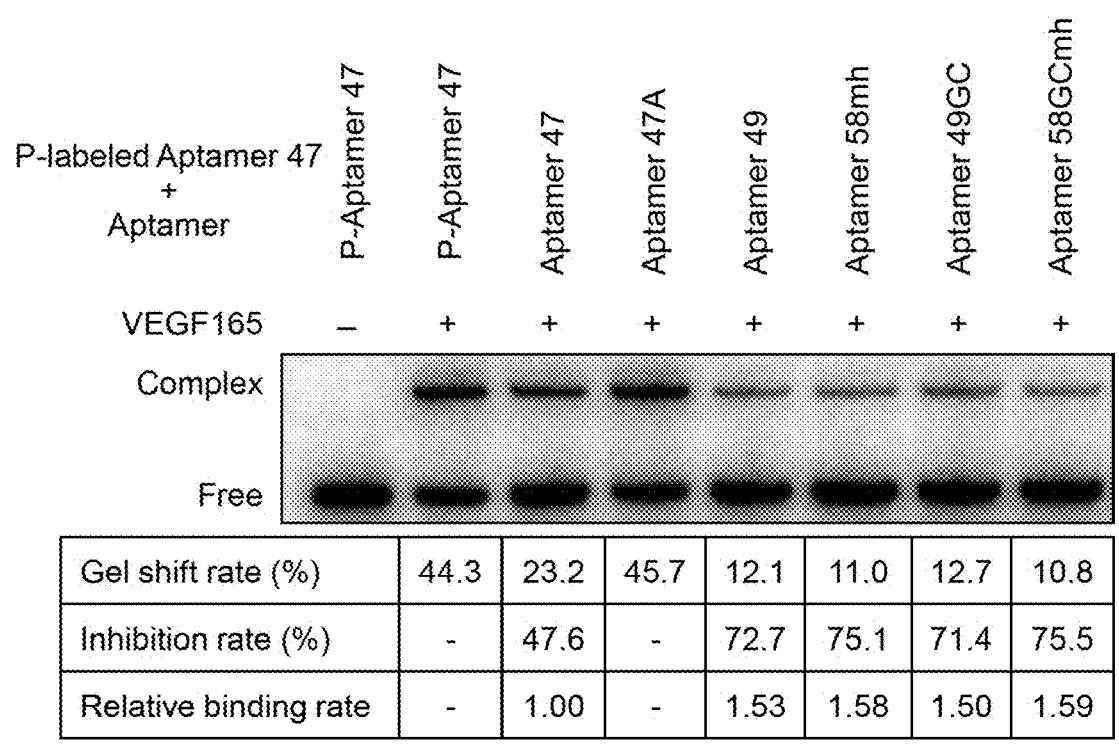
FIG. 22 is a diagram showing results of testing the competition of each aptamer for VEGF165 with Aptamer 47. The upper column shows each aptamer added together with P-labeled Aptamer 47 and the presence or absence of addition of VEGF165 (−: not added; +: added). The middle column shows the bands of a complex of P-labeled Aptamer 47 and VEGF165 and free P-labeled Aptamer 47. The lower column shows the gel shift rate, the inhibition rate of binding of Aptamer 47 to VEGF165 by each aptamer calculated from the gel shift rate, and the relative binding rate calculated by comparison with the competitive inhibitory capacity of Aptamer 47 itself.

The results are shown in FIG. 22. As shown in FIG. 22, the aptamer derived from Aptamer 47 by the substitution with A (Aptamer 47A) exhibited no inhibition of binding, whereas Aptamer 49 derived from Aptamer 47 by the elongation of the stem region by one base pair had a relative binding rate of 1.53, demonstrating that its binding strength was significantly improved. Aptamer 49GC derived from Aptamer 49 by the substitution of A-T base pairs at two sites in the stem region with G-C base pair had a relative binding rate of 1.50. On the other hand, Aptamer 58mh and Aptamer 58GCmh containing the mini-hairpin had a relative binding rate of 1.58 and 1.59, respectively, and were therefore confirmed to have improved binding strength compared with Aptamer 47, as with Aptamer 49.

Example 13: Analysis on Stability of Aptamer for VEGF in Human Serum

<Method>

In this Example, each DNA aptamer variant prepared in Example 11 was used and examined for its stability in human serum.

Each DNA aptamer containing the mini-hairpin structure (Aptamer 58mh and Aptamer 58GCmh) or each aptamer not containing this structure (Aptamer 47, Aptamer 49, and Aptamer 49GC) (final concentration: 2 µM) was mixed with human serum (Millipore Corp.) at a final concentration of 96%, and this solution was incubated at 37° C., After 0 hours, 1 hour, 6 hours, 24 hours, 48 hours, and 72 hours, 10 µL was sampled from the mixed solution, and the degradation reaction was terminated by mixing with 110 µL of 10 M urea/1×TBE. Each sample thus reacted was fractionated by 15% denaturing polyacrylamide gel electrophoresis containing 7 M urea. Then, the gel was stained with SYBR GOLD to detect a DNA fragment. The band pattern of the DNA was analyzed using Bio Imager LAS-4000 (Fujifilm Corp.). The amount of residual DNA was predicted from the density of a band corresponding to an degraded aptamer.

<Results>

Figure 23:
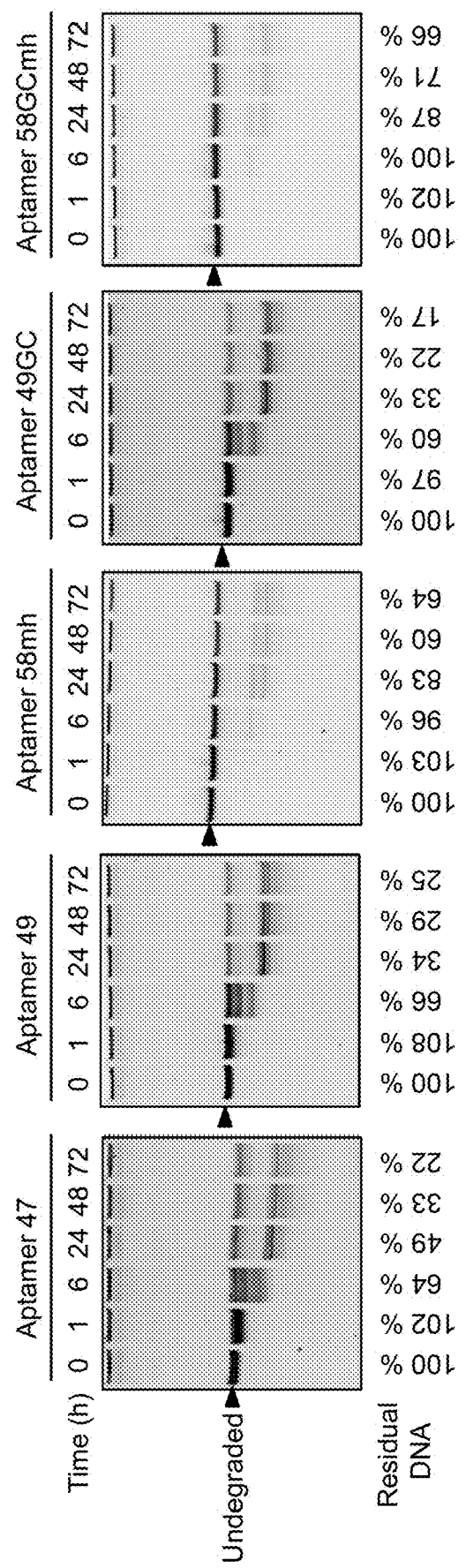
FIG. 23 is a diagram showing results of confirming the stability of each aptamer for VEGF165 in human serum by gel electrophoresis. The position of the band of an undegraded aptamer is indicated by a black triangle. Residual DNA at each time was calculated in percentage from the hand of an undegraded aptamer electrophoresed after 0 hours, 1 hours, 24 hours, 48 hours, and 72 hours.

The results are shown in FIG. 23. The band corresponding to the full-length product of each aptamer not containing the mini-hairpin structure (Aptamer 47, Aptamer 49, and Aptamer 49GC) was already 50% or less of the whole amount after 24 hours, whereas the band corresponding to the full-length product of each aptamer containing the mini-hairpin structure (Aptamer 58mh and Aptamer 58GCmh) retained 50% or more of the whole amount even after 72 hours. These results demonstrated that the mini-hairpin structure allows the aptamer to be stabilized against degradation by nucleolytic enzymes in human serum.

Example 14: Analysis on Thermal Stability of Aptamer for VEGF in Solution

<Method>

The thermal stability of each variant (Aptamer 47, Aptamer 47A, Aptamer 49, Aptamer 58mh, Aptamer 49GC, and Aptamer 58GCmh; final concentration: 2 µM in a phosphate buffer solution, pH 7.4) was studied by the measurement of a Tm value. Change in the absorbance of the DNA aptamer caused by the elevation of temperature (0.5° C./min) was measured using an ultraviolet and visible spectrophotometer UV-2450 (Shimadzu Corp.). The melting temperature (Tm value) was calculated from the first derivation thereof.

<Results>

The results are shown in FIG. 24. The control DNA aptamer (Aptamer 47) had a Tm value of 69.5° C., whereas each variant without the substitution with G-C base pairs had a Tm value of 60.0° C. (Aptamer 47A), 67.7° C. (Aptamer 49), and 65.6° C. (Aptamer 58mh). Thus, the addition of the mini-hairpin structure and G-C base pairs did not largely change the Tm value itself. As for Aptamer 49GC and Aptamer 58GCmh substituted with G-C base pairs, two phases of melting curves were obtained, and their Tm values were 54.6° C. and 78.7° C. for Aptamer 49GC and 62.6° C. and 80.8° C. for Aptamer 58GCmh. In order to further specifically examine the influence of the elongation by the G-C base pair, the substitution, and the addition of the mini-hairpin structure, melting curves up to 50° C. were enlarged and shown in the lower column of FIG. 24. It was confirmed that the change in absorbance was suppressed by the elongation by the G-C base pair (Aptamer 49) and the addition of the mini-hairpin structure (Aptamer 58mh) to stabilize the structure, and the structure was further stabilized by the substitution with G-C base pairs (Aptamer 49GC and Aptamer 58GCmh).

All of the publications, patents, and patent applications are incorporated herein by reference.

---

The invention claimed is:

1. A method for producing a DNA aptamer being stabilized and/or having enhanced capacity to bind to a target molecule, comprising the steps of:
   designing a base sequence of a DNA aptamer in accordance with a method for designing a base sequence that enhances the capacity of an existing DNA aptamer to bind to a target molecule and/or stabilizes the aptamer; and
   producing a DNA aptamer on the basis of the designed base sequence,
   wherein the method for designing a base sequence comprises
   substituting a hairpin structure consisting of one pair of stem structure and loop structure of the DNA aptamer comprising at least one stem structure and at least one loop structure with a mini-hairpin structure, wherein the stem structure is formed by base pairing of 2 or more consecutive bases constituting one strand with bases constituting another strand,
   wherein the mini-hairpin structure comprises:
   nucleic acid regions (A) to (C) below sequentially ligated from the 5' end toward the 3' end:
   (A) a first nucleic acid region comprising 2 to 5 arbitrary nucleotides;
   (B) a second nucleic acid region comprising a "gna" or "gnna" base sequence wherein each "n" independently represents either "g", "t", "a", or "c", a base analogue, or a modified base; and
   (C) a third nucleic acid region comprising a base sequence complementary to the first nucleic acid region,
   wherein the first nucleic acid region and the third nucleic acid region form a stem portion by base pairing with each other and the second nucleic acid region forms a loop portion.

2. The method according to claim 1, wherein the DNA aptamer comprises at least one base analogue and/or modified base.

3. The method according to claim 2, wherein the base analogue is 7-(2-thienyl)-3H-imidazo[4,5-b]pyridin-3-yl.

4. The method according to claim 1, comprising increasing one or more GC pairs in a stem structure other than that constituting the mini-hairpin.

5. The method according to claim 1, wherein the DNA aptamer comprises one of the at least one stem structure at the 5' and/or 3' ends thereof, wherein the method comprises increasing one to five GC pairs in the 5' and/or 3' ends of the DNA aptamer.

6. The method according to claim 1, comprising adding a further mini-hairpin structure as defined in claim 1 to one end of the DNA aptamer.

7. The method according to claim 1, wherein the difference in nucleotide length between the hairpin structure to be substituted and the mini-hairpin structure after the substitution is 3, 2, 1, or 0.

* * * * *

SEQUENCE LISTING

<160> NUMBER OF SEQ ID NOS: 24

<210> SEQ ID NO 1
<211> LENGTH: 9
<212> TYPE: DNA
<213> ORGANISM: Artificial
<220> FEATURE:
<223> OTHER INFORMATION: synthetic DNA

<400> SEQUENCE: 1 cgcgaagcg                                                          9

<210> SEQ ID NO 2
<211> LENGTH: 9
<212> TYPE: DNA
<213> ORGANISM: Artificial
<220> FEATURE:
<223> OTHER INFORMATION: synthetic DNA

<400> SEQUENCE: 2 gccgaaggc                                                          9

<210> SEQ ID NO 3
<211> LENGTH: 26
<212> TYPE: DNA
<213> ORGANISM: Artificial

```
<220> FEATURE:
<223> OTHER INFORMATION: synthetic DNA

<400> SEQUENCE: 3 gggggttggtt gtgttgggtg ttgtgt                                        26

<210> SEQ ID NO 4
<211> LENGTH: 49
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (18)..(18)
<223> OTHER INFORMATION: N is synthetic base; Ds(7-(2-
      thienyl)imidazo[4,5-b]pyridine)
<220> FEATURE:
<221> NAME/KEY: misc_feature
<222> LOCATION: (29)..(29)
<223> OTHER INFORMATION: N is synthetic base; Ds(7-(2-
      thienyl)imidazo[4,5-b]pyridine)
<220> FEATURE:
<221> NAME/KEY: misc_feature
<222> LOCATION: (40)..(40)
<223> OTHER INFORMATION: N is synthetic base; Ds(7-(2-
      thienyl)imidazo[4,5-b]pyridine)

<400> SEQUENCE: 4
tccactcggg tcatttanta atgtaggtnt gggctaggcn gctagtgga               49

<210> SEQ ID NO 5
<211> LENGTH: 49
<212> TYPE: DNA
<213> ORGANISM: Artificial
<220> FEATURE:
<223> OTHER INFORMATION: synthetic DNA

<400> SEQUENCE: 5
tccactcggg tcatttaata atgtaggtat gggctaggca gctagtgga               49

<210> SEQ ID NO 6
<211> LENGTH: 58
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (18)..(18)
<223> OTHER INFORMATION: N is synthetic base; Ds(7-(2-
      thienyl)imidazo[4,5-b]pyridine)
<220> FEATURE:
<221> NAME/KEY: misc_feature
<222> LOCATION: (29)..(29)
<223> OTHER INFORMATION: N is synthetic base; Ds(7-(2-
      thienyl)imidazo[4,5-b]pyridine)
<220> FEATURE:
<221> NAME/KEY: misc_feature
<222> LOCATION: (40)..(40)
<223> OTHER INFORMATION: N is synthetic base; Ds(7-(2-
      thienyl)imidazo[4,5-b]pyridine)

<400> SEQUENCE: 6
tccactcggg tcatttanta atgtaggtnt gggctaggcn gctagtggac gcgaagcg     58

<210> SEQ ID NO 7
<211> LENGTH: 58
<212> TYPE: DNA
<213> ORGANISM: Artificial
<220> FEATURE:
```

<223> OTHER INFORMATION: synthetic DNA
<220> FEATURE:
<221> NAME/KEY: misc_feature
<222> LOCATION: (18)..(18)
<223> OTHER INFORMATION: N is synthetic base; Ds(7-(2-
    thienyl)imidazo[4,5-b]pyridine)
<220> FEATURE:
<221> NAME/KEY: misc_feature
<222> LOCATION: (29)..(29)
<223> OTHER INFORMATION: N is synthetic base; Ds(7-(2-
    thienyl)imidazo[4,5-b]pyridine)
<220> FEATURE:
<221> NAME/KEY: misc_feature
<222> LOCATION: (40)..(40)
<223> OTHER INFORMATION: N is synthetic base; Ds(7-(2-
    thienyl)imidazo[4,5-b]pyridine)

<400> SEQUENCE: 7
cccgcccggg tcgcctantg gcgtaggtnt gggctaggcn gctggcgggc gcgaagcg    58

<210> SEQ ID NO 8
<211> LENGTH: 57
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (28)..(28)
<223> OTHER INFORMATION: N is synthetic base; Ds(7-(2-
    thienyl)imidazo[4,5-b]pyridine)
<220> FEATURE:
<221> NAME/KEY: misc_feature
<222> LOCATION: (39)..(39)
<223> OTHER INFORMATION: N is synthetic base; Ds(7-(2-
    thienyl)imidazo[4,5-b]pyridine)

<400> SEQUENCE: 8
cccgcccggg tccgcgaagc ggtaggtntg ggctaggcng ctggcgggcg cgaagcg    57

<210> SEQ ID NO 9
<211> LENGTH: 57
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (28)..(28)
<223> OTHER INFORMATION: N is synthetic base; Ds(7-(2-
    thienyl)imidazo[4,5-b]pyridine)
<220> FEATURE:
<221> NAME/KEY: misc_feature
<222> LOCATION: (39)..(39)
<223> OTHER INFORMATION: N is synthetic base; Ds(7-(2-
    thienyl)imidazo[4,5-b]pyridine)

<400> SEQUENCE: 9
tccactcggg tccgcgaagc ggtaggtntg ggctaggcng ctagtggacg cgaagcg    57

<210> SEQ ID NO 10
<211> LENGTH: 57
<212> TYPE: DNA
<213> ORGANISM: Artificial
<220> FEATURE:
<223> OTHER INFORMATION: synthetic DNA

<400> SEQUENCE: 10
cccgcccggg tccgcgaagc ggtaggtatg ggctaggcag ctggcgggcg cgaagcg    57

<210> SEQ ID NO 11

```
<211> LENGTH: 57
<212> TYPE: DNA
<213> ORGANISM: Artificial
<220> FEATURE:
<223> OTHER INFORMATION: synthetic DNA

<400> SEQUENCE: 11
tccactcggg tccgcgaagc ggtaggtatg ggctaggcag ctagtggacg cgaagcg       57

<210> SEQ ID NO 12
<211> LENGTH: 41
<212> TYPE: DNA
<213> ORGANISM: Artificial
<220> FEATURE:
<223> OTHER INFORMATION: synthetic DNA

<400> SEQUENCE: 12
ggcgtgcagt gccttcggcc gtgcggtgcc tccgtcacgc c                        41

<210> SEQ ID NO 13
<211> LENGTH: 42
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (42)..(42)
<223> OTHER INFORMATION: N is inverted dT

<400> SEQUENCE: 13
ggcgtgcagt gccttcggcc gtgcggtgcc tccgtcacgc cn                       42

<210> SEQ ID NO 14
<211> LENGTH: 41
<212> TYPE: DNA
<213> ORGANISM: Artificial
<220> FEATURE:
<223> OTHER INFORMATION: synthetic DNA

<400> SEQUENCE: 14
ggcgtgcagt gccgaaggcc gtgcggtgcc tccgtcacgc c                        41

<210> SEQ ID NO 15
<211> LENGTH: 42
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (42)..(42)
<223> OTHER INFORMATION: N is inverted dT

<400> SEQUENCE: 15
ggcgtgcagt gccgaaggcc gtgcggtgcc tccgtcacgc cn                       42

<210> SEQ ID NO 16
<211> LENGTH: 50
<212> TYPE: DNA
<213> ORGANISM: Artificial
<220> FEATURE:
<223> OTHER INFORMATION: synthetic DNA

<400> SEQUENCE: 16
ggcgtgcagt gccgaaggcc gtgcggtgcc tccgtcacgc ccgcgaagcg              50
```

<210> SEQ ID NO 17
<211> LENGTH: 47
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (24)..(24)
<223> OTHER INFORMATION: N is synthetic base; Ds(7-(2-
      thienyl)imidazo[4,5-b]pyridine)
<220> FEATURE:
<221> NAME/KEY: misc_feature
<222> LOCATION: (33)..(33)
<223> OTHER INFORMATION: N is synthetic base; Ds(7-(2-
      thienyl)imidazo[4,5-b]pyridine)

<400> SEQUENCE: 17
cggtaaactg cgtccgaagg ggcntgcagt gancccgaat gggtccg         47

<210> SEQ ID NO 18
<211> LENGTH: 47
<212> TYPE: DNA
<213> ORGANISM: Artificial
<220> FEATURE:
<223> OTHER INFORMATION: synthetic DNA

<400> SEQUENCE: 18
cggtaaactg cgtccgaagg ggcatgcagt gacccgaat gggtccg          47

<210> SEQ ID NO 19
<211> LENGTH: 49
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (25)..(25)
<223> OTHER INFORMATION: N is synthetic base; Ds(7-(2-
      thienyl)imidazo[4,5-b]pyridine)
<220> FEATURE:
<221> NAME/KEY: misc_feature
<222> LOCATION: (34)..(34)
<223> OTHER INFORMATION: N is synthetic base; Ds(7-(2-
      thienyl)imidazo[4,5-b]pyridine)

<400> SEQUENCE: 19
gcggtaaact gcgtccgaag gggcntgcag tgancccgaa tgggtccgc       49

<210> SEQ ID NO 20
<211> LENGTH: 58
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (25)..(25)
<223> OTHER INFORMATION: N is synthetic base; Ds(7-(2-
      thienyl)imidazo[4,5-b]pyridine)
<220> FEATURE:
<221> NAME/KEY: misc_feature
<222> LOCATION: (34)..(34)
<223> OTHER INFORMATION: N is synthetic base; Ds(7-(2-
      thienyl)imidazo[4,5-b]pyridine)

<400> SEQUENCE: 20
gcggtaaact gcgtccgaag gggcntgcag tgancccgaa tgggtccgcc gcgaagcg    58

<210> SEQ ID NO 21

```
<211> LENGTH: 49
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (25)..(25)
<223> OTHER INFORMATION: N is synthetic base; Ds(7-(2-
      thienyl)imidazo[4,5-b]pyridine)
<220> FEATURE:
<221> NAME/KEY: misc_feature
<222> LOCATION: (34)..(34)
<223> OTHER INFORMATION: N is synthetic base; Ds(7-(2-
      thienyl)imidazo[4,5-b]pyridine)

<400> SEQUENCE: 21
gcggtaagcc gcgtccgaag gggcntgcgg cgancccgaa tgggtccgc          49

<210> SEQ ID NO 22
<211> LENGTH: 58
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (25)..(25)
<223> OTHER INFORMATION: N is synthetic base; Ds(7-(2-
      thienyl)imidazo[4,5-b]pyridine)
<220> FEATURE:
<221> NAME/KEY: misc_feature
<222> LOCATION: (34)..(34)
<223> OTHER INFORMATION: N is synthetic base; Ds(7-(2-
      thienyl)imidazo[4,5-b]pyridine)

<400> SEQUENCE: 22
gcggtaagcc gcgtccgaag gggcntgcgg cgancccgaa tgggtccgcc gcgaagcg   58

<210> SEQ ID NO 23
<211> LENGTH: 9
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (4)..(5)
<223> OTHER INFORMATION: n is a, c, g, or t

<400> SEQUENCE: 23 gcgnnacgc                                                      9

<210> SEQ ID NO 24
<211> LENGTH: 7
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (4)..(4)
<223> OTHER INFORMATION: n is a, c, g, or t

<400> SEQUENCE: 24 gcgnagc                                                        7
```